United States Patent

Takahashi et al.

(10) Patent No.: US 8,206,310 B2
(45) Date of Patent: Jun. 26, 2012

(54) BLOOD PRESSURE MEASURING APPARATUS ENABLING ACCURATE BLOOD PRESSURE MEASUREMENT

(75) Inventors: Akihisa Takahashi, Kyoto (JP); Yoshihiko Sano, Kyoto (JP); Shingo Yamashita, Kyoto (JP); Takahide Tanaka, Otsu (JP); Yukiya Sawanoi, Nara (JP); Tomonori Inoue, Kyoto (JP); Takashi Watanabe, Kyoto (JP)

(73) Assignee: Omron Healthcare Co., Ltd., Kyoto-shi (JP)

( * ) Notice: Subject to any disclaimer, the term of this patent is extended or adjusted under 35 U.S.C. 154(b) by 1057 days.

(21) Appl. No.: 12/096,150

(22) PCT Filed: Nov. 6, 2006

(86) PCT No.: PCT/JP2006/322081
§ 371 (c)(1),
(2), (4) Date: Jun. 4, 2008

(87) PCT Pub. No.: WO2007/066461
PCT Pub. Date: Jun. 14, 2007

(65) Prior Publication Data
US 2009/0163823 A1    Jun. 25, 2009

(30) Foreign Application Priority Data

Dec. 5, 2005 (JP) ................... 2005-350937
Feb. 17, 2006 (JP) ................... 2006-041036
Apr. 28, 2006 (JP) ................... 2006-125910

(51) Int. Cl.
*A61B 5/02* (2006.01)

(52) U.S. Cl. ........................... 600/492; 600/490
(58) Field of Classification Search .............. 600/490, 600/491, 492, 495, 485, 493, 494, 496, 499, 600/500, 501, 502, 503
See application file for complete search history.

(56) References Cited

U.S. PATENT DOCUMENTS

| | | | |
|---|---|---|---|
| 6,224,558 B1 * | 5/2001 | Clemmons | 600/490 |
| 6,336,901 B1 | 1/2002 | Itonaga et al. | |
| 6,589,185 B1 * | 7/2003 | Archibald et al. | 600/494 |
| 2005/0182332 A1 | 8/2005 | Sano et al. | |

FOREIGN PATENT DOCUMENTS

EP      1566143      8/2005

(Continued)

OTHER PUBLICATIONS

Japanese Decision to Grant Patent, mailed May 19, 2009, directed to Japanese Patent Application No. 2006-125910; 6 pages.

(Continued)

*Primary Examiner* — Miranda Le
*Assistant Examiner* — Tho Tran
(74) *Attorney, Agent, or Firm* — Morrison & Foerster LLP

(57) ABSTRACT

A blood pressure measuring apparatus controls a winding mechanism in parallel with increase or decrease of a pressure of a measuring fluid bladder after the measuring fluid bladder is wound around a measurement region. Therefore, a change in a winding state of the measuring fluid bladder is prevented. Additionally, measurement accuracy is improved by keeping compliance of the measuring fluid bladder constant.

13 Claims, 23 Drawing Sheets

FOREIGN PATENT DOCUMENTS

| | | |
|---|---|---|
| EP | 1 591 061 | 11/2005 |
| EP | 1 958 565 A1 | 8/2008 |
| JP | 5-269089 | 10/1993 |
| JP | 6-014889 | 1/1994 |
| JP | 11-309119 | 11/1999 |
| JP | 11-318835 | 11/1999 |
| JP | 3113737 | 9/2000 |
| JP | 2004-174029 | 6/2004 |
| JP | 2004-215847 | 8/2004 |
| JP | 2005-230175 | 9/2005 |
| RU | 2 281 687 | 8/2006 |
| WO | WO-2007/066461 A1 | 6/2007 |

OTHER PUBLICATIONS

Supplementary European Search Report mailed Jan. 22, 2010, directed to corresponding European Patent Application No. 06822995.4; 6 pages.

International Search Report mailed Nov. 28, 2006, directed at counterpart PCT application No. PCT/JP2006/322081; 2 pages.

Russian Decision on Grant mailed Nov. 12, 2009, directed to corresponding Russian Patent Application No. 2008127308/14(033475); 12 pages.

Russian Office Action mailed Jun. 15, 2009 directed to corresponding application No. 2008127308/14(033475); (10 pages).

* cited by examiner

BLOOD PRESSURE MEASURING APPARATUS ENABLING ACCURATE BLOOD PRESSURE MEASUREMENT

CROSS REFERENCE TO RELATED APPLICATIONS

This application is a national stage application under 35 USC 371 of International Application No. PCT/JP2006/322081, filed Nov. 6, 2006, which claims the priority of Japanese Application Nos. 2005-350937, filed Dec. 5, 2005; 2006-041036, filed Feb. 17, 2006; and, 2006-125910, filed Apr. 28, 2006, the contents of which are incorporated herein by reference.

TECHNICAL FIELD

The present invention relates to a blood pressure measuring apparatus, and particularly to a blood pressure measuring apparatus in which a cuff can be fixed to a living body.

BACKGROUND ART

When a blood pressure is measured, a cuff functioning as an ischemic band including a fluid bladder for blood pressure measurement is wound around a part of a living body and fixed, and then a pressure of the fluid bladder is increased or reduced. A technique, in which a change in volume of a compressed blood vessel is captured as a change in amplitude of a fluctuation in cuff pressure by increasing or decreasing the pressure of the cuff wound around a part of the living body and the blood pressure is computed, is called an oscillometric method.

In an electronic blood-pressure meter in which the oscillometric method is adopted, when the state of the cuff pressure is changed, the amplitude of the fluctuation in cuff pressure generated by the change in volume of the blood vessel is also changed. Even in the same cuff pressure, when the volume of the cuff is changed, the amplitude of the fluctuation in cuff pressure is changed. That is, depending on softness of a measurement region (such as upper arm) to be measured, a size (circumferential length) of the measurement region, and a cuff winding state, the amplitude of a pressure pulse wave is changed when the cuff volume is changed although an artery is compressed with the same cuff pressure. Specifically, the pressure pulse wave is decreased as the cuff volume is increased, while the pressure pulse wave is increased as the cuff volume is decreased. That is, the amplitude of the pressure pulse wave is changed according to measurement states except for the information on the blood pressure of the living body, and the large cuff volume is required to increase the cuff pressure to the same level when the measurement region has the large size or when the living body is soft. Therefore, the pressure pulse wave amplitude used to compute the blood pressure is changed depending on the measurement state, which influences measurement accuracy. In order to suppress an error caused by the measurement state except for the information on the blood pressure of the living body, Japanese Patent No. 3113737 (hereinafter, referred to as Patent Document 1) discloses an electronic blood-pressure meter in which the a characteristic of the change in cuff volume to the cuff pressure is previously provided to convert a signal of the change in cuff pressure into the change in cuff volume and a blood pressure value is measured using the converted cuff volume.

When the cuff is fixed with an insufficient force, the fluid bladder is inflated outside without compressing the blood vessel during pressurization, and the fluid bladder does not effectively fulfill an original role in pressing and closing the blood vessel, which results in deterioration of accuracy of blood pressure measurement. When the winding state is changed during the pressurization, accuracy of blood pressure estimation performed during the pressurization is largely deteriorated. Accordingly, after the cuff is wound around the living body, it is necessary that the winding state be securely fixed to suppress an error.

The following configurations fixing the cuff are well known. There is well known a configuration in which the cuff winding state is maintained by a surface fastener. In a blood pressure measuring apparatus in which the cuff is automatically wound around the living body to measure the blood pressure, for example, Japanese Patent Laying-Open No. 2004-215847 (hereinafter, referred to as Patent Document 2) discloses a lock mechanism engaging a slide unit to become immobile at a wind end position in a mechanism in which one end of the cuff is pulled by a slide mechanism to wind the cuff around a part of the living body, and Japanese Patent Laying-Open No. 6-14889 (hereinafter, referred to as Patent Document 3) discloses a lock engaged with a wind-up mechanism at the end of winding to prevent reverse rotation in a mechanism in which the cuff is wound around a part of the living body by winding up a rope connected to the cuff.

Japanese Patent Laying-Open No. 2005-230175 (hereinafter, referred to as Patent Document 4), previously applied by the inventor, discloses a blood pressure measuring apparatus having a configuration in which, unlike the configuration of the usual blood pressure measuring apparatus, two fluid bladders independently provided with a curler interposed therebetween are used for winding of the cuff and the blood pressure measurement.

As to the configuration of the blood pressure measuring apparatus in which the two fluid bladders independently provided with a curler interposed therebetween are used for winding of the cuff and the blood pressure measurement, Japanese patent Laying-Open No. 11-309119 (hereinafter, referred to as Patent Document 5) and Japanese Patent Laying-Open No. 11-318835 (hereinafter, referred to as Patent Document 6) disclose a configuration in which pressing means for supplying a predetermined amount of fluid to a compressing fluid bladder compressing a human body and pressing the compressing fluid bladder against the living body is provided. Japanese Patent Laying-Open No. 5-269089 (hereinafter, referred to as Patent Document 7) discloses a configuration in which a small inner cuff compressing an artery is filled with a low-viscosity conduction solution and the inner cuff is pressed against the human body by an outer cuff located outside the inner cuff.

A measuring operation shown in FIG. 12 is performed in the blood pressure measuring apparatus having the configuration disclosed in Patent Document 4. Referring to FIG. 12, initialization is performed in Step S1, and the measuring air bladder functioning as the measuring fluid bladder is compressed against the blood pressure measuring part through the curler by supplying air to a compressing and fixing bag functioning as the compressing fluid bladder in Step S2. When a pressure of the measuring air bladder reaches a predetermined pressure, it is determined that the measuring air bladder is wound around the blood pressure measuring part, and the pressurization is ended in Step S3. In Step S4, the living body is compressed to pressurize the measuring air bladder functioning as the air bladder for measuring the blood pressure to a pressure enough to press and close the blood vessel. In Step S5, an artery pressure pulse wave and a pressure value are detected while the pressure is reduced. In Step S6, the blood pressure is computed based on the artery pressure pulse wave and the pressure value. The measurement result is displayed in Step S7, and the air in the compressing and fixing air bladder and the measuring air bladder is vented to release the compression of the living body in Step S8.

Referring to FIGS. 13 to 16, the pressurization and depressurization operations of the compressing and fixing air bladder and the measuring air bladder during the measuring operation will be described in detail.

FIG. 13 is a schematic view for illustrating the pressurization and depressurization operations of the compressing and fixing air bladder and the measuring air bladder in Steps S2 and S3. Referring to FIG. 13, at the start of the measurement, the compressing and fixing air bladder is in the non-pressurized state in which the compressing and fixing air bladder is released to an atmospheric air and the compressing and fixing air bladder is in the compressive state. Then, a predetermined amount of air is supplied to the measuring air bladder, and the compressing and fixing air bladder is preliminarily pressurized.

FIG. 14 is a schematic view for illustrating the pressurization and depressurization operations of the compressing and the fixing air bladder and measuring air bladder in Step S4. Referring to FIG. 14, the internal pressure of the measuring air bladder preliminarily pressurized in Steps S2 and S3 and the change in internal pressure reach predetermined values, the supply of the air to the compressing and fixing air bladder is ended, and the air is supplied to the measuring air bladder to pressurize the measuring air bladder in Step S4. When the air is supplied to the measuring air bladder to pressurize the measuring air bladder, the measuring air bladder is inflated inside in a radial direction because an outer circumference is fixed by a housing, and the curler is pressed in an inner diameter direction. Therefore, the measuring air bladder provided inside the curler is pressed against the measurement region.

FIG. 15 is a schematic view for illustrating the pressurization and depressurization operations of the measuring air bladder in Step S5. Referring to FIG. 15, when the air is supplied to the measuring air bladder to reach the internal pressure enough to press and close the artery in Step S4, the supply of the air is ended, and the air of the measuring air bladder is discharged to depressurize in Step S5. When the pressure is reduced, the pressing force acting on the artery is weakened. In Step S5, the internal pressure of the measuring air bladder is measured at that time to detect the artery pressure pulse wave.

FIG. 16 is a view showing fluctuations in internal pressures of the compressing and fixing air bladder and measuring air bladder in first to fourth procedures. In FIG. 16, the first procedure (I) is a procedure for preliminarily pressurizing the measuring air bladder, the second procedure (II) is a procedure for pressurizing the compressing and fixing air bladder in Step S2, the third procedure (III) is a procedure for pressurizing the measuring air bladder in Step S4, and the fourth procedure (IV) is a procedure for depressurizing the measuring air bladder in Step S5.

Referring to FIG. 16, in the first procedure, because the compressing and fixing air bladder is in the non-compressive state, the internal pressure of the compressing and fixing air bladder becomes substantially zero, and a predetermined amount of air is preliminarily supplied to the measuring air bladder to detect winding. When the predetermined amount of air is preliminarily supplied to the measuring air bladder, the supply of the air is ended, and then the pressurization of the compressing and fixing air bladder is started as the second procedure.

In the second procedure, the internal pressure of the measuring air bladder and the change in internal pressure are monitored, and the compressing and fixing air bladder is pressurized until the internal pressure of the measuring air bladder and the change in internal pressure reach predetermined values.

Then, in the third procedure, the measuring air bladder is pressurized while the internal pressure of the compressing and fixing air bladder is maintained. When the measuring air bladder reaches the pressure enough to press and close the artery, the pressure of the measuring air bladder is reduced in the fourth procedure.

Patent Document 1: Japanese Patent No. 3113737
Patent Document 2: Japanese Patent Laying-Open No. 2004-215847
Patent Document 3: Japanese Patent Laying-Open No. 6-14889
Patent Document 4: Japanese Patent Laying-Open No. 2005-230175
Patent Document 5: Japanese Patent Laying-Open No. 11-309119
Patent Document 6: Japanese Patent Laying-Open No. 11-318835
Patent Document 7: Japanese Patent Laying-Open No. 5-269089

DISCLOSURE OF THE INVENTION

Problems to be Solved by the Invention

It is necessary to previously give the pressure of the cuff and a characteristic of the change in volume, in the conventional measurement method disclosed in Patent Document 1 in which the oscillometric method is adopted for the electronic blood-pressure meter. However, unfortunately correction cannot sufficiently be performed, because the characteristic of the change in volume is infinitely changed depending on the measurement state such as the cuff winding manner, the circumferential length of the measurement region, and softness of the living body. In a case where a plurality of complicated corrections are demanded using flow rate detection, detection of the circumferential length of the measurement region, detection of the winding state, and detection of the softness of the living body, unfortunately a need of a large-scale apparatus is impractically raised.

Because the blood pressure measuring apparatus described in Patent Document 4 differs largely from the usual blood pressure measuring apparatus in the configuration, it is difficult to apply the mechanism for fixing the cuff. Therefore, in the blood pressure measuring apparatus described in Patent Document 4, unfortunately it is difficult to properly fix the measuring fluid bladder corresponding to the cuff. That is, sometimes the small amount of fluid is supplied to the compressing and fixing fluid bladder depending on the state of the measurement region (such as a circumferential length of the measurement region). In such cases, sometimes the change in internal pressure of the compressing and fixing fluid bladder and the change in internal pressure of the measuring fluid bladder become shown in FIG. 17. In the third procedure, when the measuring fluid bladder is pressurized, sometimes the internal pressure of the measuring fluid bladder exceeds the internal pressure of the compressing and fixing fluid bladder (enclosed portion in FIG. 17). As a result, as shown in FIG. 18, the pressure inflating the measuring fluid bladder to compress the curler from the inner circumferential side becomes dominant compared with the pressure compressing the curler from the outer circumferential side, which results in a problem in that the measuring fluid bladder is not properly pressed against the measurement region because the curler is spread outside in the radial direction. Additionally, when the large amount of fluid is supplied to the measuring fluid bladder, unfortunately the pressure pulse wave is hardly detected. These problems possibly cause deterioration of the accuracy of blood pressure measurement.

Furthermore, a long time is required for the measuring operation with increasing amount of fluid supplied to the measuring fluid bladder.

When the compressing fluid bladder having the constant volume is pressed toward the measurement region to perform the compression, the volume of the measuring fluid bladder is changed according to the pressing force. In the case of the low pressing force, the volume of the fluid bladder is increased and the pressure pulse wave generated from the living body becomes small. On the other hand, the pressure pulse wave becomes large in the case of the high pressing force. Particularly, a volume ratio of the pressure becomes large when the measuring fluid bladder detecting the pressure pulse wave has the small volume. Therefore, unfortunately sometimes the pressure pulse wave is easily deformed to deteriorate the accuracy of blood pressure measurement.

A difference in size of the pressure pulse wave is generated by the circumferential length of the measurement region, which results in a problem in that the accuracy of blood-pressure measurement is deteriorated. That is, because the cuff volume is changed by the measurement state such as the circumferential length of the measurement region during the measurement, the pressure pulse wave generated from the change in cuff pressure caused by the change in volume of the blood vessel depends on the measurement state, which results in the problem in that the accuracy of blood-pressure measurement is deteriorated.

In view of the foregoing, a first object of the present invention is to provide a blood pressure measuring apparatus having a configuration in which the measuring fluid bladder and the function of winding the fluid bladder provided with the curler interposed therebetween are used, wherein the measuring fluid bladder can properly be fixed to the living body to improve the accuracy of blood pressure measurement.

A second object of the present invention is to provide a blood pressure measuring apparatus in which the change in relationship between the internal pressure and volume of the measuring fluid bladder can be suppressed irrespective of the measurement state to improve the accuracy of blood pressure measurement.

Means for Solving the Problems

In accordance with an aspect of the present invention, a blood pressure measuring apparatus includes a measuring fluid bladder corresponding to a measuring air bladder 13 in the following embodiments; a supply means corresponding to a pump 21, a valve 22, a pump driving circuit 26, and valve driving circuit 27 in the following embodiments for supplying a fluid to the measuring fluid bladder; a measuring fluid bladder compressing means corresponding to a compressing and fixing air bladder 8 and a wire 81 in the following embodiments for compressing the measuring fluid bladder in a direction of a measurement region; a sensor corresponding to a pressure sensor 23 in the following embodiments for measuring an internal pressure of the measuring fluid bladder; a compression degree detection means corresponding to a pressure sensor 33 in the following embodiments for measuring a compression degree of the measuring fluid bladder compressed by the measuring fluid bladder compressing means; and a first control means corresponding to a CPU (Central Processing Unit) 40 in the following embodiments for controlling the compression degree of the measuring fluid bladder by the measuring fluid bladder compressing means, wherein, assuming that a first procedure is a procedure of supplying a predetermined amount of fluid to the measuring fluid bladder at start of measurement, a second procedure is a procedure of compressing the measuring fluid bladder against the measurement region to a predetermined compression degree by the measuring fluid bladder compressing means after the first procedure, and a third procedure is a procedure of supplying a fluid to the measuring fluid bladder and then discharging the fluid after the second procedure, the first control means controls the compression degree by the measuring fluid bladder compressing means based on the internal pressure of the measuring fluid bladder in the third procedure. The first and second procedures correspond to first and second procedures shown in FIG. 7, and the third process corresponds to third and fourth procedures shown in FIG. 7.

Preferably, the first control means controls the compression degree by the measuring fluid bladder compressing means based on information indicating a change in internal pressure of the measuring fluid bladder and information indicating a change in supply amount of the fluid in the supply means in the third procedure.

Preferably, the third procedure includes a first step corresponding to the third procedure shown in FIG. 7 of supplying a fluid to the measuring fluid bladder to pressurize the measuring fluid bladder and a second step corresponding to the fourth procedure shown in FIG. 7 of discharging the fluid to depressurize the measuring fluid bladder, and the first control means controls the compression degree by the measuring fluid bladder compressing means such that an internal pressure level of the measuring fluid bladder is not larger than the compression degree by the measuring fluid bladder compressing means in the first step.

Alternatively, the third procedure preferably includes a first step corresponding to the third procedure shown in FIG. 7 of supplying a fluid to the measuring fluid bladder to pressurize the measuring fluid bladder and a second step corresponding to the fourth procedure shown in FIG. 7 of discharging the fluid to depressurize the measuring fluid bladder, and the first control means controls the compression degree by the measuring fluid bladder compressing means such that an internal pressure level of the measuring fluid bladder is not smaller than the compression degree by the measuring fluid bladder compressing means in the second step.

Alternatively, the first control means preferably controls the compression degree by the measuring fluid bladder compressing means such that a volume of the measuring fluid bladder is kept constant.

Alternatively, the first control means preferably controls the compression degree by the measuring fluid bladder compressing means such that compliance of the measuring fluid bladder is kept constant. Specifically, the measuring fluid bladder compressing means preferably controls the compression degree such that the compression degree by the measuring fluid bladder compressing means is increased in a process of pressurizing the measuring fluid bladder and/or the compression degree by the measuring fluid bladder compressing means is decreased in a process of depressurizing the measuring fluid bladder. As used herein, the term of compliance shall mean a numerical value indicating the change in volume of the measuring fluid bladder to the change in pressure of the measuring fluid bladder. Assuming that $\Delta V$ is the change in volume of the measuring fluid bladder when the internal pressure of the measuring fluid bladder is changed by $\Delta P$, a compliance Cp for an internal pressure P of the measuring fluid bladder is expressed by $Cp=\Delta V/\Delta P$.

Preferably, the first control means estimates a circumferential length of the measurement region from the information indicating the change in internal pressure of the measuring fluid bladder in the second procedure, and the first control means controls the compression degree in the measuring fluid bladder compressing means according to the circumferential length of the measurement region based on the change in internal pressure of the measuring fluid bladder in the third procedure. Specifically, in the following embodiments, it is assumed that a relationship shown in FIG. 8 holds between the change in internal pressure of the measuring fluid bladder and the winding state ("tight winding" and "loose winding") of the measuring air bladder. Assuming that the measuring fluid bladder is tightly wound in the case of the fast pressurization speed, preferably the first control means performs the control such that the compression degree is decreased in the measuring fluid bladder compressing means. Assuming that the measuring fluid bladder is loosely wound in the case of the slow pressurization speed, preferably the first control means performs the control such that the compression degree is increased in the measuring fluid bladder compressing means.

Preferably, the measuring fluid bladder compressing means is a compressing and fixing fluid bladder corresponding to a compressing and fixing air bladder 8 in the following embodiments located on a side farther away from the measurement region of the measuring fluid bladder while a flexible member corresponding to a curler 10 in the following embodiments is interposed.

Preferably, the first control means estimates a circumferential length of the measurement region from the information indicating the change in internal pressure of the measuring fluid bladder in the second procedure, and the first control means controls the compression degree by the measuring fluid bladder compressing means according to the circumferential length of the measurement region in the second procedure when estimating that the circumferential length is larger than a predetermined value. Specifically, the control is preferably performed such that a difference between the compression degree by the measuring fluid bladder compressing means and an internal pressure level of the measuring fluid bladder in the second procedure is larger than a difference between the compression degree by the measuring fluid bladder compressing means and an internal pressure level of the measuring fluid bladder in the third procedure.

Preferably, the blood pressure measuring apparatus further includes a second control means for controlling supply of the fluid in the supply means, wherein the second control means estimates a circumferential length of the measurement region from the information indicating the change in internal pressure of the measuring fluid bladder in the second procedure, and the second control means controls such that the supply means supplies an amount of fluid corresponding to the circumferential length of the measurement region in the second procedure when estimating that the circumferential length is smaller than a predetermined value. Specifically, the amount corresponding to the circumferential length of the measurement region is preferably a difference between an amount of fluid supplied to the measuring fluid bladder in the third procedure when the circumferential length has the predetermined value, that is, when the thickness of the measurement region is medium, and an amount of fluid supplied to the measuring fluid bladder in the third procedure when the circumferential length is the estimated circumferential length, that is, when the thickness of the measurement region is smaller than the medium size.

EFFECTS OF THE INVENTION

In the blood pressure measuring apparatus according to the present invention, after the measuring fluid bladder compressing means presses the measuring fluid bladder against the measurement region, the compression degree of the measuring fluid bladder is controlled by the measuring fluid bladder compressing means based on the internal pressure of the measuring fluid bladder. Therefore, the measuring fluid bladder can properly be fixed to the measurement region, and the accuracy of blood pressure measurement can be improved.

In the structure of the blood pressure measuring apparatus according to the present invention, the compression degree by the measuring fluid bladder compressing means is changed according to the circumferential length of the measurement region, and the volume of the measuring fluid bladder is controlled so as to be kept constant irrespective of the circumferential length of the measurement region, whereby the measuring fluid bladder having the constant volume is compressed against the living body. Therefore, the change in relationship between the measuring fluid bladder internal pressure and the volume of the measuring fluid bladder can be suppressed irrespective of the measurement state (such as softness of the living body, the circumferential length of the measurement region, the winding method). Accordingly, the change in compliance caused by the internal pressure of the measuring fluid bladder is suppressed to a constant level to improve the accuracy of blood pressure measurement.

DESCRIPTION OF THE REFERENCE SIGNS 1 blood-pressure meter, 2 main body, 3 manipulation part, 4 display, 5 measuring part, 6 housing, 7 cover, 13 measuring air bladder, 10 curler, 8 compressing and fixing air bladder, 20 measuring air system, 23 and 33 pressure sensor, 21 and 31 pump, 22 and 32 valve, 26 and 36 pump driving circuit, 27 and 37 valve driving circuit, 28 and 38 amplifier, 29 and 39 A/D converter, 30 compressing and fixing air system, 40 CPU, 41 memory, 81 wire, 82 wire wind-up part, 100 upper arm

BEST MODES FOR CARRYING OUT THE INVENTION

Embodiments of the present invention will be described below with reference to the drawings. In the following description, the same component and constituent are designated by the same numeral, and the same component and constituent have the same name and the same function.

Figure 1:
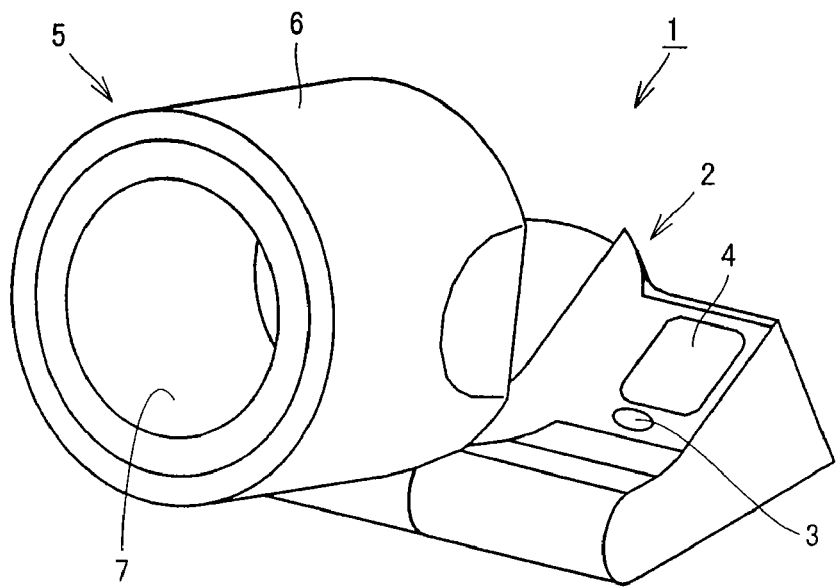
FIG. 1 is a perspective view showing an example of an appearance of a blood-pressure meter 1.

Referring to FIG. 1, a blood pressure measuring apparatus (hereinafter, referred to as blood-pressure meter) 1 according to the present embodiment mainly includes a main body 2 placed on a desk or the like, and a measuring part 5 for allowing an upper arm serving as a measurement region to be inserted thereinto. A manipulation part 3, a display 4, and an elbow holder are provided in an upper portion of main body 2. A power button and a measurement button are placed in manipulation part 3. Measuring part 5 is attached to main body 2 while an angle of measuring part 5 is variable with respect to main body 2, and measuring part 5 includes a housing 6 and a living body compressing and fixing apparatus. Housing 6 is a substantially cylindrical frame, and the living body compressing and fixing apparatus is accommodated in an inner circumferential portion of housing 6. As shown in FIG. 1, the living body compressing and fixing apparatus accommodated in the inner circumferential portion of housing 6 is not exposed in a normal usage state, but is covered with a cover 7.

Figure 2:
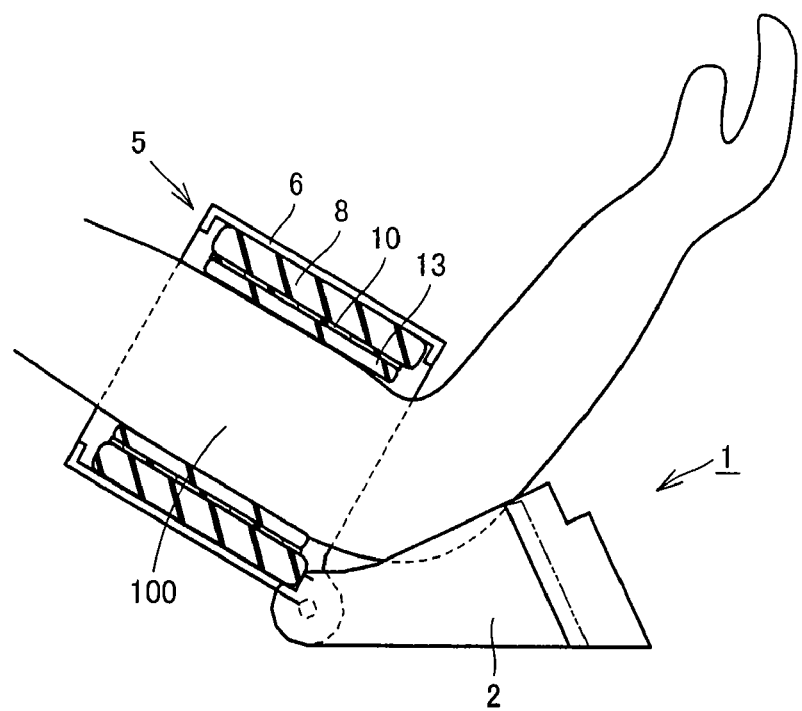
FIG. 2 is a schematic sectional view showing the blood-pressure meter 1 in measuring a blood pressure.

Referring to FIG. 2, in measuring the blood pressure, an upper arm 100 is inserted into housing 6 to place an elbow on the elbow holder, and an instruction is made to start measurement. Upper arm 100 is compressed and fixed by the living body compressing and fixing apparatus to measure the blood pressure.

The living body compressing and fixing apparatus includes a measuring air bladder 13, a curler 10, and a compressing and fixing air bladder 8. Measuring air bladder 13 functioning as the measuring fluid bladder compresses the measurement region corresponding to the cuff to measure blood pressure. Curler 10 functioning as the flexible member is located outside measuring air bladder 13, and curler 10 has a substantially cylindrical shape which can be expanded and contracted in a radial direction. Compressing and fixing air bladder 8 functioning as the measuring fluid bladder compressing means is located outside curler 10. Compressing and fixing air bladder 8 is inflated to press an outer circumferential surface of curler 10 toward the inside, thereby reducing a diameter of curler 10. Compressing and fixing air bladder 8 presses measuring air bladder 13 against the measurement region of the living body through curler 10 along with housing 6.

Figure 3:
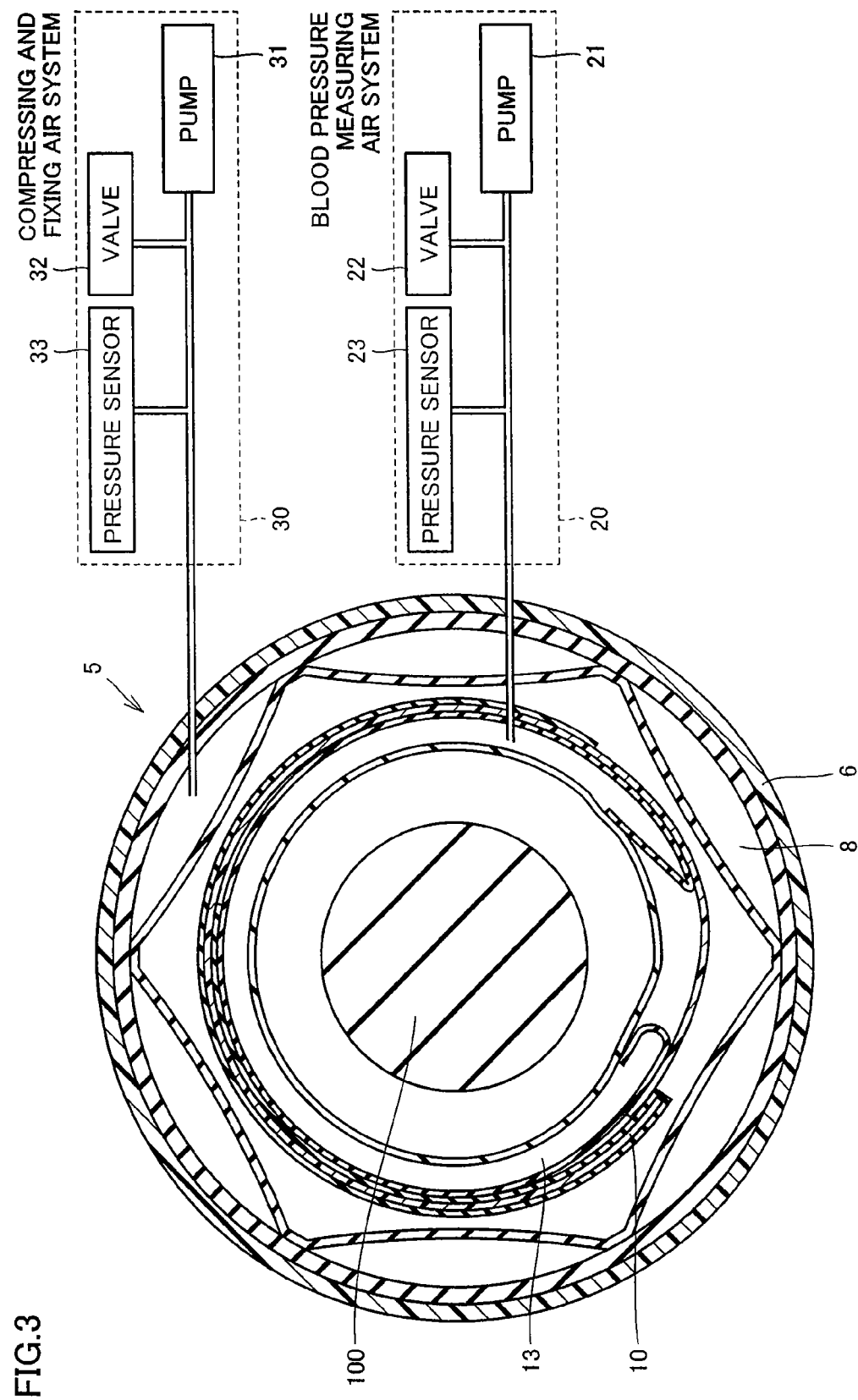
FIG. 3 is a sectional view for illustrating an internal structure of a measuring part 5.
Figure 4:
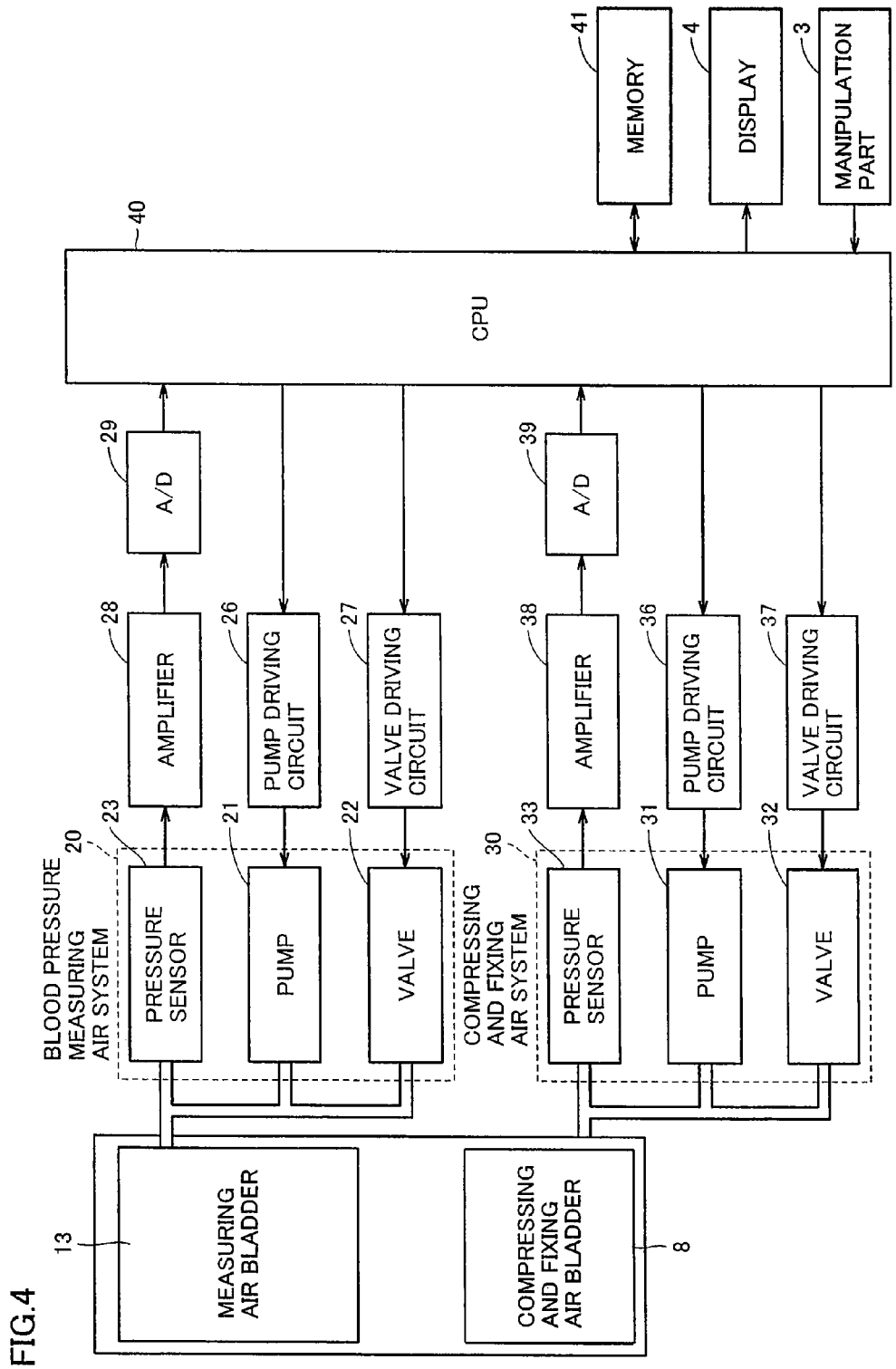
FIG. 4 is a block diagram showing a specific example of a functional configuration of the blood-pressure meter 1.

Referring to FIG. 3, in measuring part 5, compressing and fixing air bladder 8 is provided inside housing 6, and compressing and fixing air bladder 8 is inflated and reduced by a compressing and fixing air system 30 (see FIG. 4).

Curler 10 formed by a plate-shape member wound in the substantially cylindrical shape is disposed inside compressing and fixing air bladder 8, and curler 10 is elastically deformed in the radial direction by application of an external force. Measuring air bladder 13 is disposed inside curler 10, and is inflated and reduced by a measuring air system 20 (see FIG. 4) to be described later.

Referring to FIG. 4, blood-pressure meter 1 includes measuring air bladder 13 and compressing and fixing air bladder 8, and measuring air bladder 13 and compressing and fixing air bladder 8 are connected to measuring air system 20 and compressing and fixing air system 30 respectively. Measuring air system 20 includes a pressure sensor 23 measuring the internal pressure of measuring air bladder 13, a pump 21 supplying and discharging air to and from measuring air bladder 13, and a valve 22. Compressing and fixing air system 30 includes a pressure sensor 33 measuring the internal pressure of compressing and fixing air bladder 8, a pump 31 supplying and discharging air to and from compressing and fixing air bladder 8, and a valve 32.

Blood-pressure meter 1 also includes CPU (Central Processing Unit) 40 controlling the whole of blood-pressure meter 1, an amplifier 28, a pump driving circuit 26, and a valve driving circuit 27 which are connected to measuring air system 20, an amplifier 38, a pump driving circuit 36, and a valve driving circuit 37 which are connected to compressing and fixing air bladder 8, A/D (Analog to Digital) converters 29 and 39 connected to amplifiers 28 and 38 respectively, a memory 41 in which programs executed by CPU 40 and measurement result are stored, display 4 displaying the measurement result and the like, and manipulation part 3 including the measurement start button and the power button.

CPU 40 executes a predetermined program stored in memory 41 based on a manipulation signal inputted from manipulation part 3, and outputs a control signal to pump driving circuits 26 and 36 and valve driving circuits 27 and 37. Pump driving circuits 26 and 36 and valve driving circuits 27 and 37 drive pumps 21 and 31 and valves 22 and 32 according to the control signal to perform the blood pressure measuring operation.

Pressure sensor 23 detects the internal pressure of measuring air bladder 13, and inputs a detection signal to amplifier 28. Pressure sensor 33 corresponding to the compression degree detection means detects the internal pressure of compressing and fixing air bladder 8, and pressure sensor 33 inputs the detection signal to amplifier 38. The internal pressure of compressing and fixing air bladder 8 corresponds to the compression degree of the measuring fluid bladder compressed by the measuring fluid bladder compressing means. The inputted pressure signals are respectively amplified to predetermined amplitudes by amplifiers 28 and 38 and converted into digital signals by A/D converters 29 and 39, and the digital signals are inputted to CPU 40.

CPU 40 performs a predetermined process based on the internal pressures of measuring air bladder 13 and compressing and fixing air bladder 8 which are obtained from pressure sensors 23 and 33, and CPU 40 outputs the control signal to pump driving circuits 26 and 36 and valve driving circuits 27 and 37 according to the process result. CPU 40 refers to a blood pressure value based on the internal pressure of measuring air bladder 13 obtained from pressure sensor 23, and CPU 40 outputs the measurement result to display the same on display 4.

Figure 5:
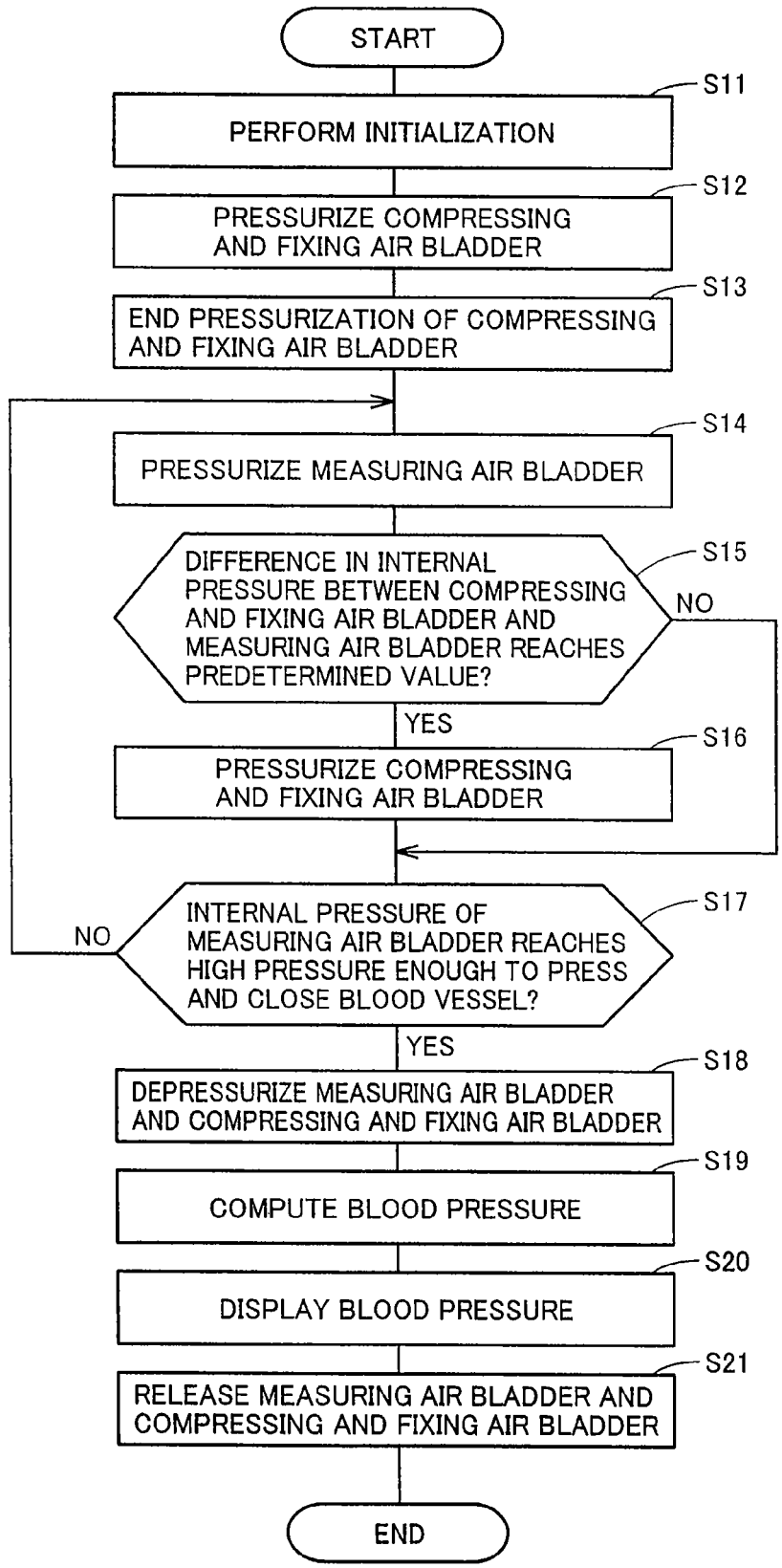
FIG. 5 is a flowchart showing a blood pressure measuring operation of the blood-pressure meter 1.

CPU 40 reads and executes the program stored in memory 41, and controls each unit shown in FIG. 4, thereby realizing a blood pressure measuring operation shown in a flowchart of FIG. 5 performed by blood-pressure meter 1.

Referring to FIG. 5, in Step S11, after initialization is performed, a predetermined amount of air is supplied to measuring air bladder 13 to preliminarily pressurize measuring air bladder 13. In Step S12, the pressurization of compressing and fixing air bladder 8 is started. At this point, CPU 40 monitors the internal pressure of measuring air bladder 13 obtained from pressure sensor 23 and the change in internal pressure. When the internal pressure of measuring air bladder 13 and the change in internal pressure reach predetermined values, the pressurization is ended in Step S13.

In Step S14, pressurization of measuring air bladder 13 is started. At this point, CPU 40 monitors the internal pressure of measuring air bladder 13 obtained from pressure sensor 23 and the internal pressure of compressing and fixing air bladder 8 obtained from pressure sensor 33, and CPU 40 determines whether or not a difference between the internal pressures reaches a predetermined value. Specifically, the predetermined value is a value not lower than about 30 mmHg, and preferably a value of about 50 mmHg. Preferably the predetermined value is set according to a material characteristic of curler 10 such as a material and a frictional force of a surface of curler 10 and a shape characteristic such as a radius. The predetermined value may previously set, or the predetermined value may be set by computation from a predetermined ratio to the internal pressure of compressing and fixing air bladder 8 at that time.

When CPU 40 determines that the difference between the internal pressure of measuring air bladder 13 and the internal pressure of compressing and fixing air bladder 8 obtained from pressure sensor 33 reaches the predetermined value (YES in Step S15), CPU 40 outputs the control signal to pump driving circuit 36 and valve driving circuit 37 to start the pressurization of compressing and fixing air bladder 8 (Step S16).

The pressurization of measuring air bladder 13 and the pressurization of compressing and fixing air bladder 8 are performed until the internal pressure of measuring air bladder 13 reaches a pressure enough to press and close the blood vessel (YES in Step S17). Then, in Step S18, the depressurization of measuring air bladder 13 is started. At this point, similarly to the pressurization, CPU 40 monitors the difference between the internal pressure of measuring air bladder 13 obtained from pressure sensor 23 and the internal pressure of compressing and fixing air bladder 8 obtained from pressure sensor 33, and CPU 40 also reduces the internal pressure of compressing and fixing air bladder 8 such that the difference is maintained with respect to a predetermined ratio to the internal pressure of compressing and fixing air bladder 8.

In Step S19, CPU 40 computes the blood pressure based on the internal pressure and pressure pulse wave of measuring air bladder 13, which are obtained from pressure sensor 23 during pressurization of measuring air bladder 13 in Step S14 or during the depressurization of measuring air bladder 13 in Step S17. In Step S20, CPU 40 causes display 4 to display the blood pressure. In Step S21, the air of compressing and fixing air bladder 8 and the air of measuring air bladder 13 are vented to release the compression of the living body.

As to the method for controlling the relationship between the internal pressure of measuring air bladder 13 and the internal pressure of compressing and fixing air bladder 8 during the blood pressure measurement, CPU 40 obtains the internal pressure of measuring air bladder 13 from pressure sensor 23 after proper winding of measuring air bladder 13

Figure 22:
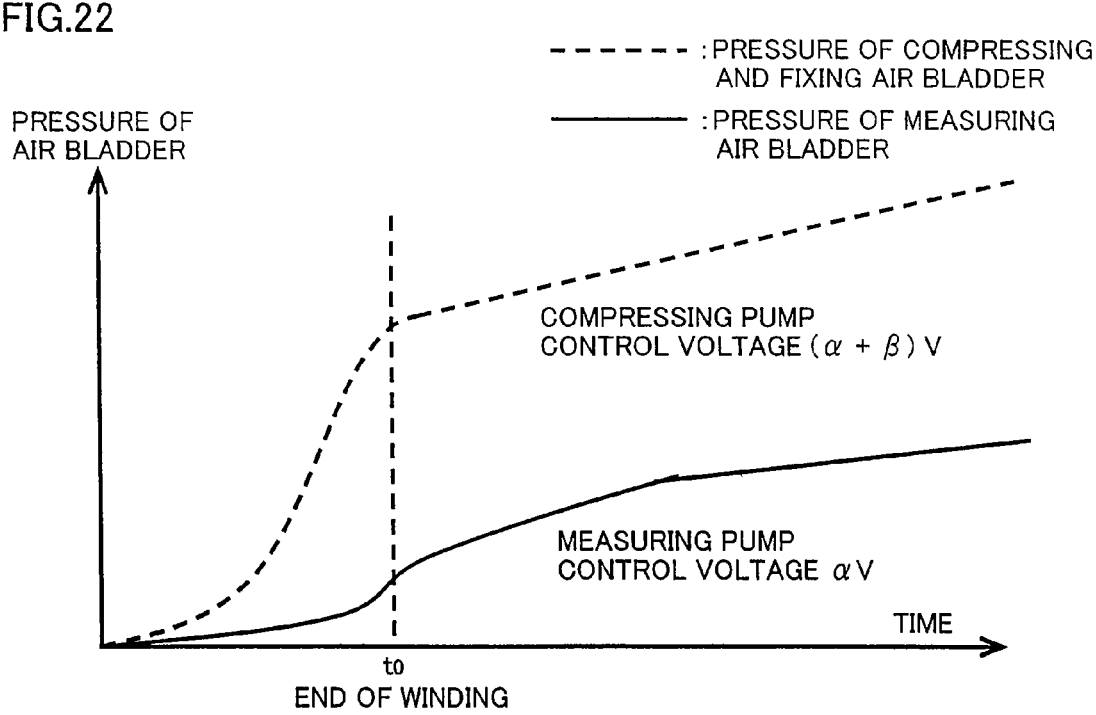
FIG. 22 is a view showing time changes of internal pressures of the compressing and fixing air bladder 8 and measuring air bladder 13.

(end of winding), and CPU 40 may control pump driving circuit 36 based on the obtained value such that the internal pressure of compressing and fixing air bladder 8 becomes a predetermined pressure. Specifically, in the case where the control is performed in pressurizing measuring air bladder 13, CPU 40 refers to time changes of the internal pressures of measuring air bladder 13 and compressing and fixing air bladder 8 shown in FIG. 22 to obtain a driving voltage a of pump driving circuit 26 (or valve driving circuit 27) supplying (or discharging) the air to measuring air bladder 13, and CPU 40 may drive pump driving circuit 36 (or valve driving circuit 37) with a start-up voltage ($\alpha+\beta$) in which a predetermined voltage $\beta$ is added to the driving voltage $\alpha$. In the present invention, the predetermined voltage $\beta$ is not limited to a particular value, but the predetermined voltage $\beta$ is preferably determined by a thickness of the measurement region, the current internal pressure of measuring air bladder 13, or compliance of measuring air bladder 13.

Figure 6:
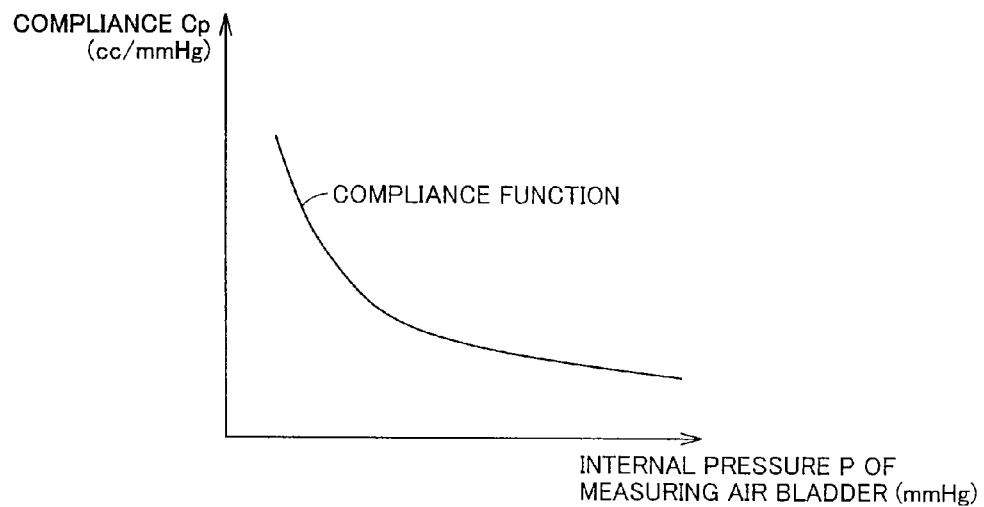
FIG. 6 is a schematic view illustrating a relationship between compliance Cp and an internal pressure P of a measuring air bladder 13.
Figure 19:
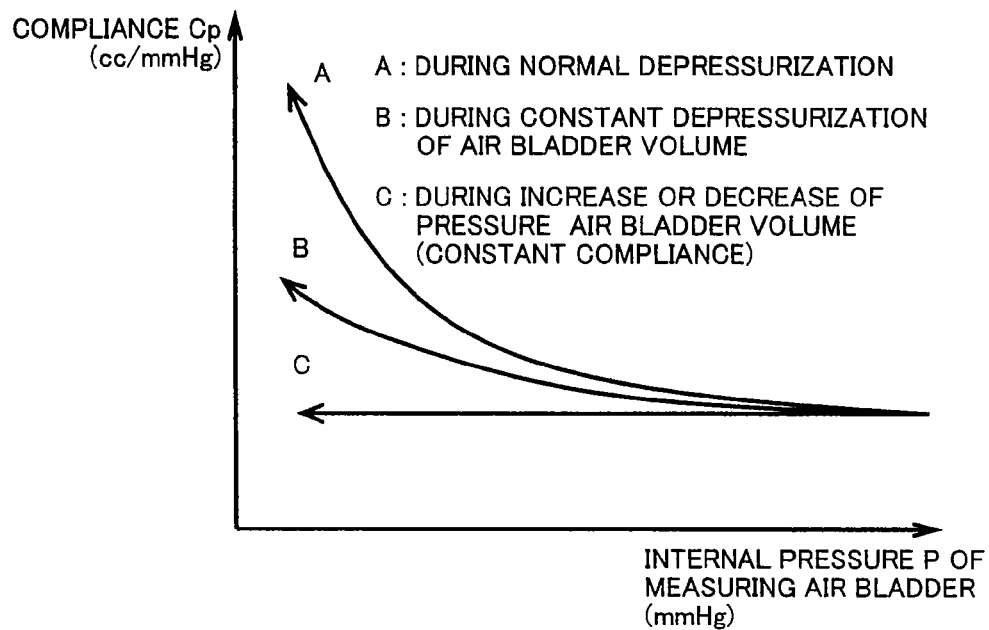
FIG. 19 is a schematic view illustrating a relationship between compliance Cp and an internal pressure P of measuring air bladder 13 when a volume of measuring air bladder 13 is changed in reducing internal pressure P of measuring air bladder 13.

In blood-pressure meter 1 according to the present embodiment, CPU 40 performs the control to keep the internal pressure of compressing and fixing air bladder 8 optimum in Steps S16 and S18. Specifically, preferably CPU 40 performs the control such that the volume of measuring air bladder 13 is kept constant as much as possible, such that the compliance is kept constant as much as possible, and such that the relationship with the internal pressure of measuring air bladder 13 is kept constant. As used herein, the term of compliance shall mean a numerical value indicating the change in volume of measuring air bladder 13 to the change in pressure of measuring air bladder 13. Assuming that $\Delta V$ is the change in volume of measuring air bladder 13 when the internal pressure of measuring air bladder 13 is changed by $\Delta P$, compliance Cp for an internal pressure P of measuring air bladder 13 is expressed by $Cp=\Delta V/\Delta P$. Compliance Cp is a function of internal pressure P of measuring air bladder 13. Because the volume of measuring air bladder 13 becomes small when measuring air bladder 13 has the low internal pressure P, it is necessary that the larger amount of air be discharged compared with the large volume (high internal pressure P) of measuring air bladder 13 in order to lower the internal pressure of measuring air bladder 13 by a predetermined amount. Therefore, as shown in FIG. 6, compliance Cp is increased as internal pressure P of measuring air bladder 13 becomes lower. The compliance function depends on the thickness or softness of the measurement region (upper arm), the cuff winding manner, and the material characteristic (such as elastic force) of measuring air bladder 13. In Steps S16 and S18, preferably CPU 40 performs the control such that the change in compliance shown in FIG. 6 is suppressed as much as possible to keep the compliance constant. As shown in FIG. 19, in the case where the volume of measuring air bladder 13 is changed in reducing internal pressure P of measuring air bladder 13, when the volume of measuring air bladder 13 is kept constant (B) in reducing internal pressure P of measuring air bladder 13 from the relationship between compliance Cp and internal pressure P of measuring air bladder 13, the change in compliance is suppressed to a smaller level compared with the normal depressurization (A) in which the volume of measuring air bladder 13 is decreased with reducing the internal pressure. When the internal pressure is reduced while the volume of measuring air bladder 13 is increased (C), the compliance can further be kept constant. Obviously, compliance Cp can further be kept constant in pressurizing internal pressure P of measuring air bladder 13 when the internal pressure is pressurized while the volume of measuring air bladder 13 is decreased. That is, preferably CPU 40 controls the amount of air supplied to (or discharged from) measuring air bladder 13, and CPU 40 increases the volume to keep compliance Cp constant in reducing internal pressure P of measuring air bladder 13 and/or CPU 40 decreases volume in reducing internal pressure P of measuring air bladder 13.

The influence of the change in compliance can be removed from the measurement result by performing the control, and the measurement accuracy can be improved in blood-pressure meter 1.

Figure 7:
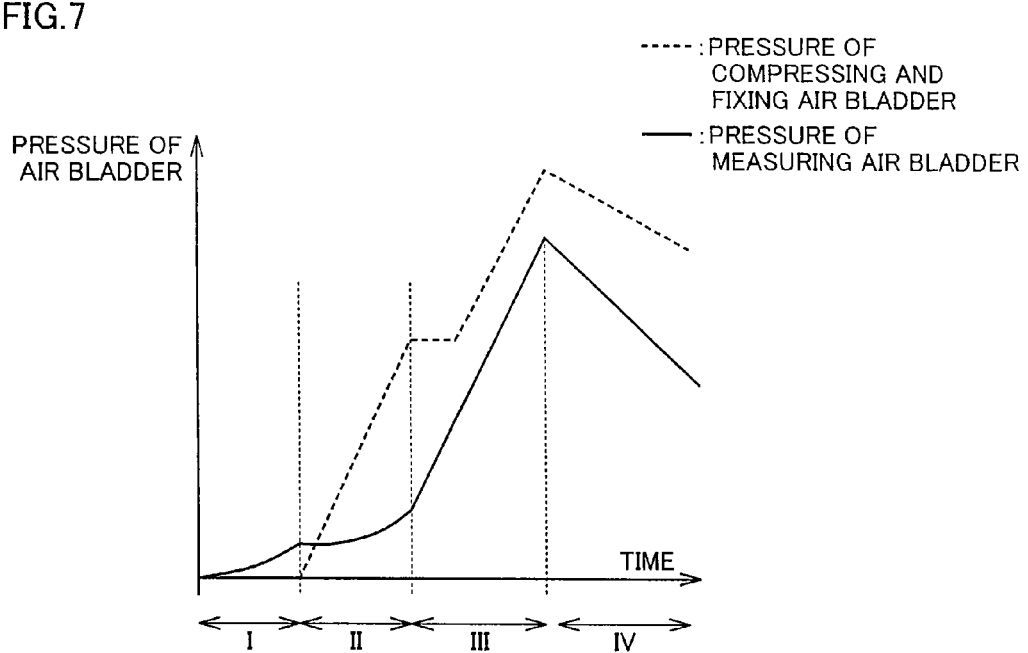
FIG. 7 is a view showing fluctuations in internal pressures of a compressing and fixing air bladder 8 and measuring air bladder 13 in first to fourth procedure.

In the blood pressure measuring operation performed by blood-pressure meter 1, it is assumed that the first procedure (I) is a procedure for preliminarily pressurizing measuring air bladder 13, the second procedure (II) is a procedure for pressurizing compressing and fixing air bladder 8 in Step S12, the third procedure (III) is a procedure for pressurizing measuring air bladder 13 in Step S14, and the fourth procedure (IV) is a procedure for reducing the internal pressure of compressing and fixing air bladder 8 in Step S18. FIG. 7 is a view showing fluctuations in internal pressures of compressing and fixing air bladder 8 and measuring air bladder 13 in the first to fourth procedure.

Referring to FIG. 7, in blood-pressure meter 1, in the second procedure, the air is supplied to compressing and fixing air bladder 8 to pressurize compressing and fixing air bladder 8 until the internal pressure of measuring air bladder 13 and the change in internal pressure reach the predetermined values, i.e., until a space between curler 10 and the measurement region becomes the proper volume. Then, curler 10 is pressed inside in the radial direction against the measurement region.

In the third procedure, the internal pressure of measuring air bladder 13 is monitored when the supply of the air to measuring air bladder 13 is started, and the supply of the air to compressing and fixing air bladder 8 is started at the time when the internal pressure of measuring air bladder 13 reaches the predetermined pressure. CPU 40 computes the amount of air supplied to compressing and fixing air bladder 8 according to the pressurized state of measuring air bladder 13. CPU 40 controls the pressurization of compressing and fixing air bladder 8 such that a predetermined relationship holds between the internal pressure of measuring air bladder 13 and the internal pressure of compressing and fixing air bladder 8.

Similarly, in the fourth procedure for reducing the internal pressure of measuring air bladder 13 after the internal pressure reaches the predetermined pressure, CPU 40 computes the amount of air discharged from compressing and fixing air bladder 8 according to the depressurization state of measuring air bladder 13. CPU 40 controls depressurization of compressing and fixing air bladder 8 such that a predetermined relationship holds between the internal pressure of measuring air bladder 13 and the internal pressure of compressing and fixing air bladder 8.

Figure 17:
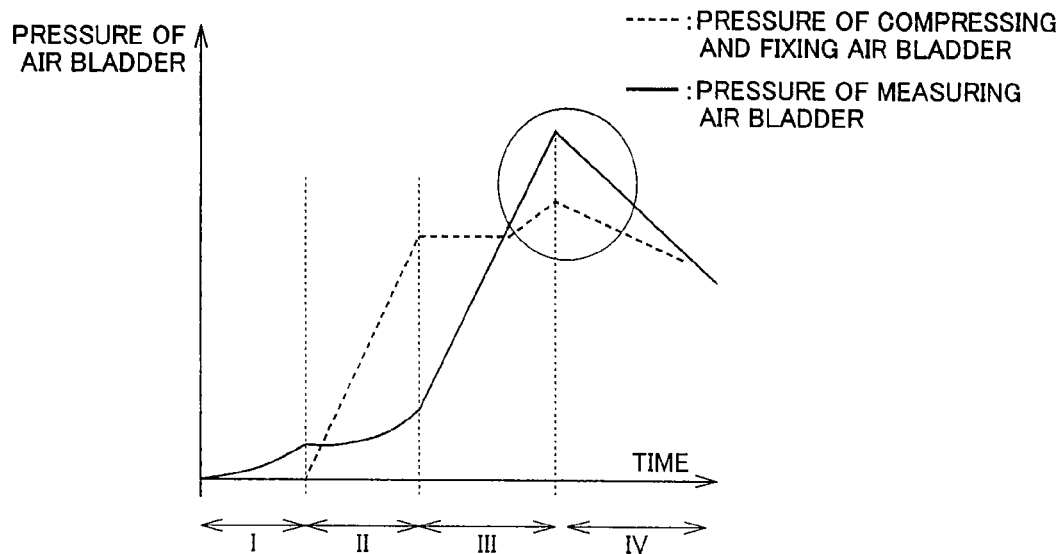
FIG. 17 is a schematic view showing a change in internal pressure of the compressing and fixing air bladder and a change in internal pressure of the measuring air bladder.
Figure 18:
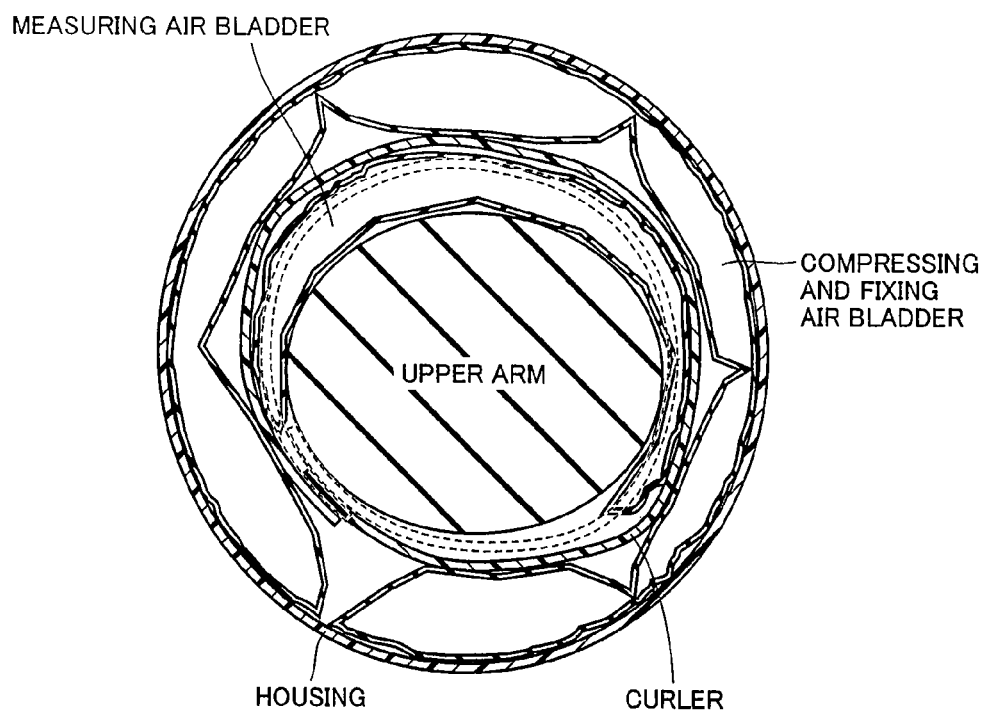
FIG. 18 is a schematic view for illustrating the pressurization and depressurization operations of the compressing and fixing air bladder and measuring air bladder.

That the internal pressure of measuring air bladder 13 exceeds the internal pressure of compressing and fixing air bladder 8 as shown in FIG. 17 can be prevented in the third and fourth procedures by performing the control in blood-pressure meter 1 according to the present embodiment. Accordingly, the situation in which curler 10 is expanded outside in the radial direction as described with reference to FIG. 18 can be prevented to properly press measuring air bladder 13 against the measurement region. This enables the accuracy of blood pressure measurement to be enhanced.

Figure 20:
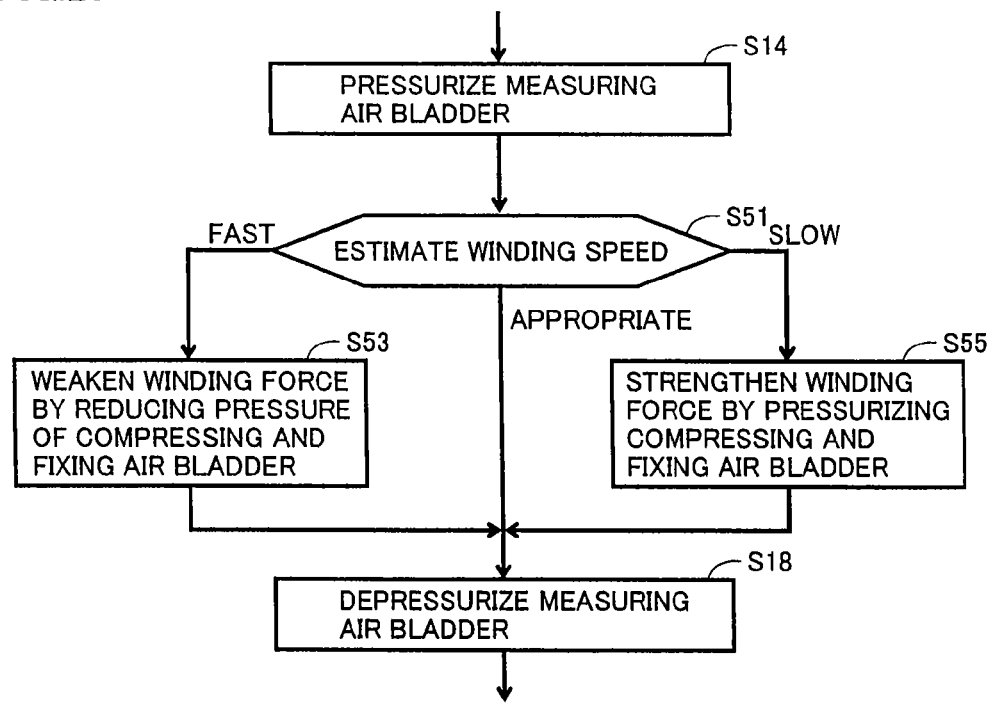
FIG. 20 is a flowchart showing a process of adjusting a winding state of measuring air bladder 13.

A process shown in a flowchart of FIG. 20 may be performed by CPU 40 when measuring air bladder 13 is pressurized in Step S14.

Referring to FIG. 20, when the pressurization of measuring air bladder 13 is started in Step S14, CPU 40 performs a process of evaluating a winding speed of measuring air bladder 13 in Step S51. Specifically, CPU 40 estimates the circumferential length of the measurement region based on a time necessary for the pressurization of measuring air bladder 13. For example, a correlation between the time necessary for pressurization and the circumferential length of the measurement region is previously stored such that the measurement region has the circumferential length of 30 cm when the time necessary for the pressurization is 5 sec and such that the measurement region has the circumferential length of 25 cm when the time necessary for the pressurization is 10 sec. The circumferential length of the measurement region can be measured using the previously stored correlation. CPU 40 computes the driving voltage of pump 21 to realize a target pressurization speed (for example, 6 mmHg/sec) for pressurizing measuring air bladder 13 based on the estimated circumferential length of the measurement region. CPU 40 outputs the control signal to pump driving circuit 26 based on the computation result. For example, the driving voltage of 6V of pump 21 is computed when the measurement region has the circumferential length of 30 cm, and the driving voltage of 5V of pump 21 is computed when the measurement region has the circumferential length of 25 cm. Alternatively, a correlation between the circumferential length of the measurement region and the driving voltage of pump 21 may previously be stored to compute the driving voltage necessary for pump 21 using the correlation.

When the pressurization of measuring air bladder 13 is started in Step S14, CPU 40 obtains the change in internal pressure of measuring air bladder 13 at an early procedure (for example, a procedure for pressurizing from 20 mmHg to 40 mmHg), CPU 40 confirms whether or not measuring air bladder 13 is properly wound by the compression of compressing and fixing air bladder 8 in Step S12. When measuring air bladder 13 is appropriately wound ("appropriate" in Step S51), the target pressurization speed can be realized. In the case where CPU 40 determines that measuring air bladder 13 is properly wound although measuring air bladder 13 is not properly wound due to the influence of movement of the body during the winding operation, the winding state is evaluated by confirming the pressurization speed of measuring air bladder 13, which allows the winding state to be corrected.

Figure 8:
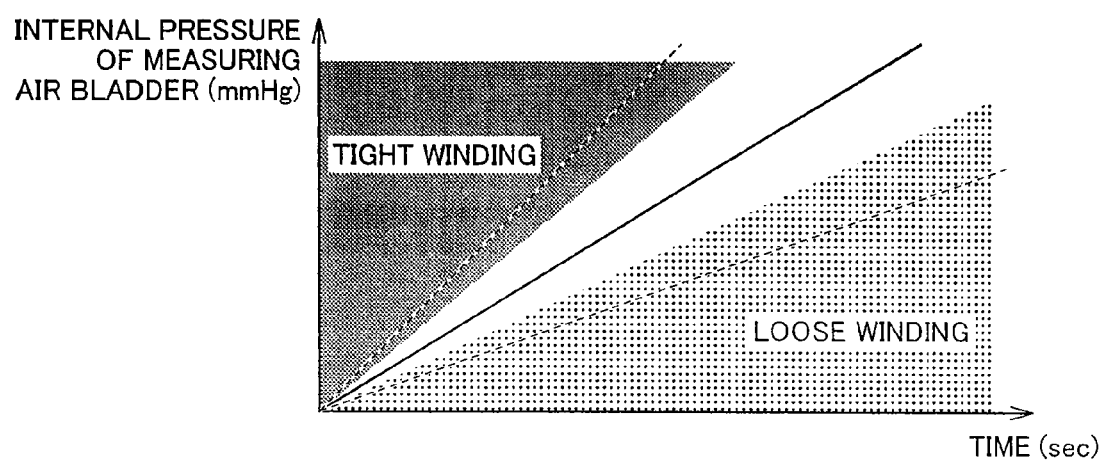
FIG. 8 is a schematic view showing a relationship between a change in internal pressure of measuring air bladder 13 and a winding state of measuring air bladder 13.
Figure 9A:
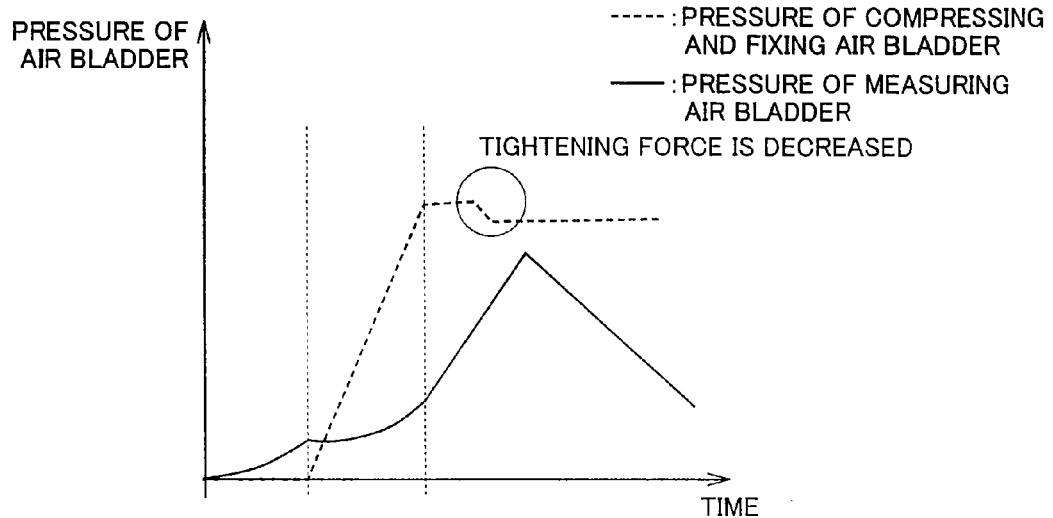
FIG. 9A is a schematic view showing a change in internal pressure of measuring air bladder 13 and a change in internal pressure of the compressing and fixing air bladder 8.

A relationship between the change in internal pressure of measuring air bladder 13 and the winding state of measuring air bladder 13 will specifically be described with reference to FIG. 8. In FIG. 8, a vertical axis indicates the internal pressure of measuring air bladder 13 obtained from pressure sensor 23, and a horizontal axis indicates an elapsed time corresponding to a driving time of pump 21. In the case where the change in internal pressure of measuring air bladder 13 is larger than a range (region of a graph portion including a solid line of FIG. 8) of a standard amount of change (for example, in the case where the pressurization speed is not lower than 7 mmHg/sec) ("fast" in Step S51), namely, in the case where the internal pressure of measuring air bladder 13 exists in the region indicated by a "tight winding" region in FIG. 8, CPU 40 estimates from these values that measuring air bladder 13 excessively compresses the measurement region because measuring air bladder 13 is not properly wound around the measurement region ("tight winding"). In Step S53, CPU 40 outputs the control signal to pump driving circuit 36 to reduce the internal pressure of compressing and fixing air bladder 8 according to the change in internal pressure of measuring air bladder 13. FIG. 9A shows the changes in internal pressures of measuring air bladder 13 and compressing and fixing air bladder 8 when the control in Step S53 is performed.

Figure 9B:
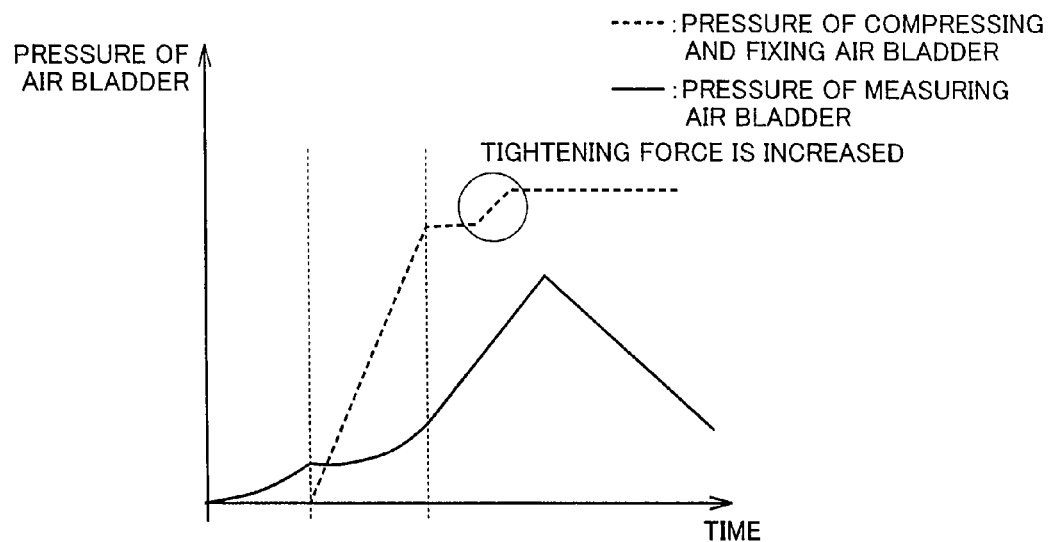
FIG. 9B is a schematic view showing the change in internal pressure of measuring air bladder 13 and the change in internal pressure of the compressing and fixing air bladder 8.

On the other hand, in the case where the change in internal pressure of measuring air bladder 13 is smaller than the range of the standard amount of change ("slow" in Step S51), namely, in the case where the internal pressure of measuring air bladder 13 exists in the region indicated by a "loose winding" region in FIG. 8 (for example, in the case where the pressurization speed is not more than 5 mmHg/sec), CPU 40 estimates that measuring air bladder 13 excessively weakly compresses the measurement region because measuring air bladder 13 is not properly wound around the measurement region ("loose winding"). In Step S55, CPU 40 outputs the control signal to pump driving circuit 36 to pressurize compressing and fixing air bladder 8 according to the change in internal pressure of measuring air bladder 13. FIG. 9B shows the changes in internal pressures of measuring air bladder 13 and compressing and fixing air bladder 8 when the control in Step S55 is performed.

CPU 40 of blood-pressure meter 1 according to the present embodiment performs the above-described control to adjust the pressing force acting on curler 10 by compressing and fixing air bladder 8, even after compressing and fixing air bladder 8 is pressurized to wind measuring air bladder 13 corresponding to the cuff around the measurement region and start the pressurization of measuring air bladder 13. Therefore, tight winding of measuring air bladder 13 due to the excessively small space between curler 10 and the measurement region and loose winding of measuring air bladder 13 due to the excessively large space between curler 10 and the measurement region can be prevented irrespective of the thickness (circumferential length) of the measurement region. Accordingly, measuring air bladder 13 corresponding to the cuff can properly be pressed against the measurement region.

Figure 10A:
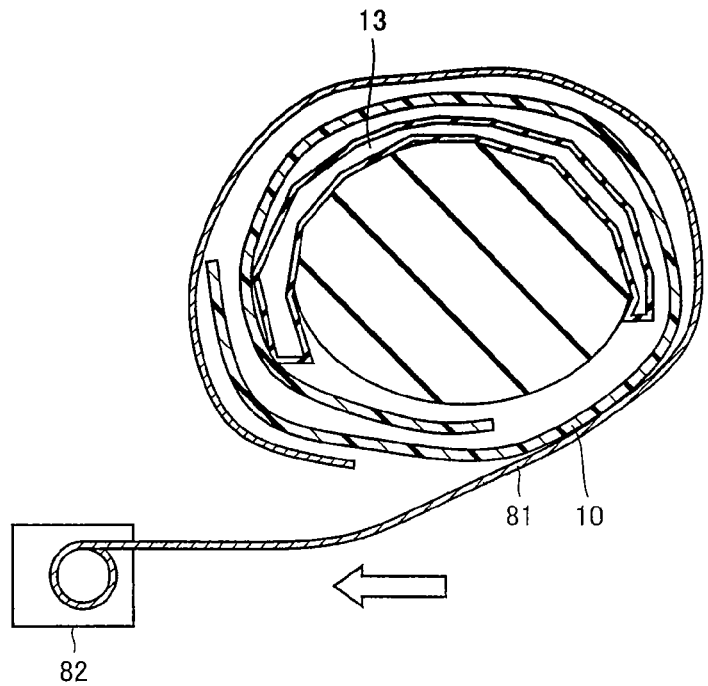
FIG. 10A is a view illustrating a mechanism pressing measuring air bladder 13 against a measurement region in a blood-pressure meter according to a modification.
Figure 10B:
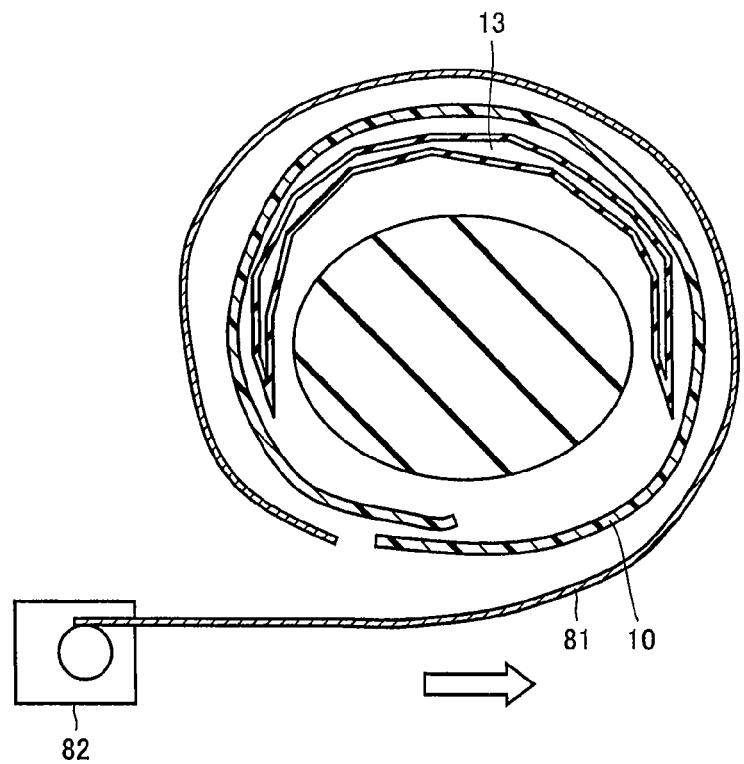
FIG. 10B is a view illustrating the mechanism pressing measuring air bladder 13 against the measurement region in the blood-pressure meter according to the modification.

The measuring fluid bladder compressing means pressing measuring air bladder 13 against the measurement region through curler 10 is not limited to the compressing and fixing air bladder, but any mechanism may be used as long as the mechanism includes the similar function. Specifically, as shown in FIGS. 10A and 10B, blood-pressure meter 1 according to a modification may includes a wire 81 and a wire wind-up part 82 instead of compressing and fixing air bladder 8. Wire 81 presses measuring air bladder 13 against the measurement region through curler 10, and wire wind-up part 82 is a mechanism driving a wire wind-up driving circuit (not shown) corresponding to pump driving circuit 36 to wind up wire 81. Measuring air bladder 13 may be pressed against the measurement region through curler 10 by tightening of wire 81 wound up by wire wind-up part 82 as shown in FIG. 10A, and the compression of measuring air bladder 13 pressed against the measurement region may be released by rewinding wire 81 delivered from wire wind-up part 82 as shown in FIG. 10B.

Figure 11:
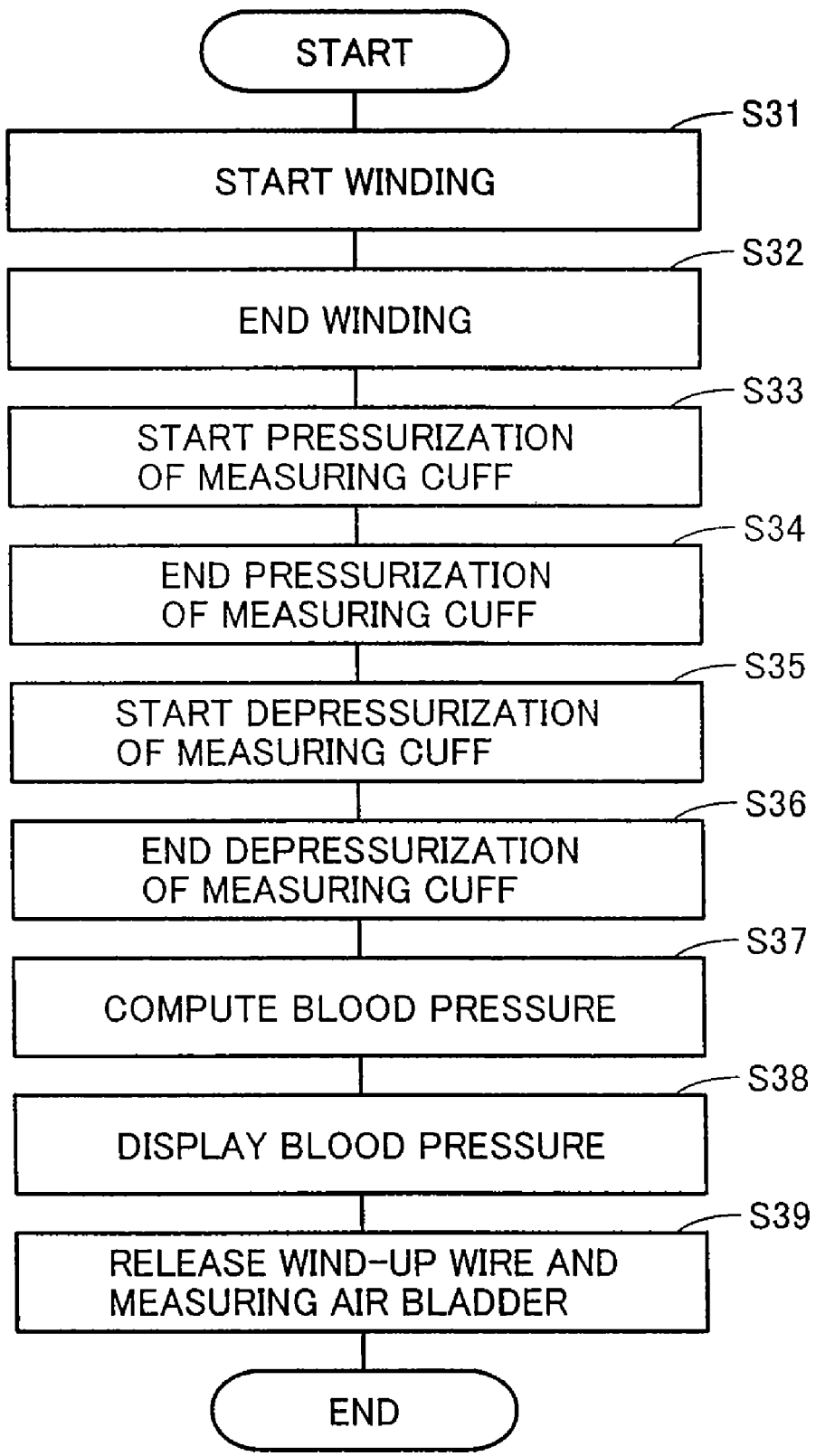
FIG. 11 is a flowchart showing a blood pressure measuring operation of the blood-pressure meter according to the modification.
Figure 12:
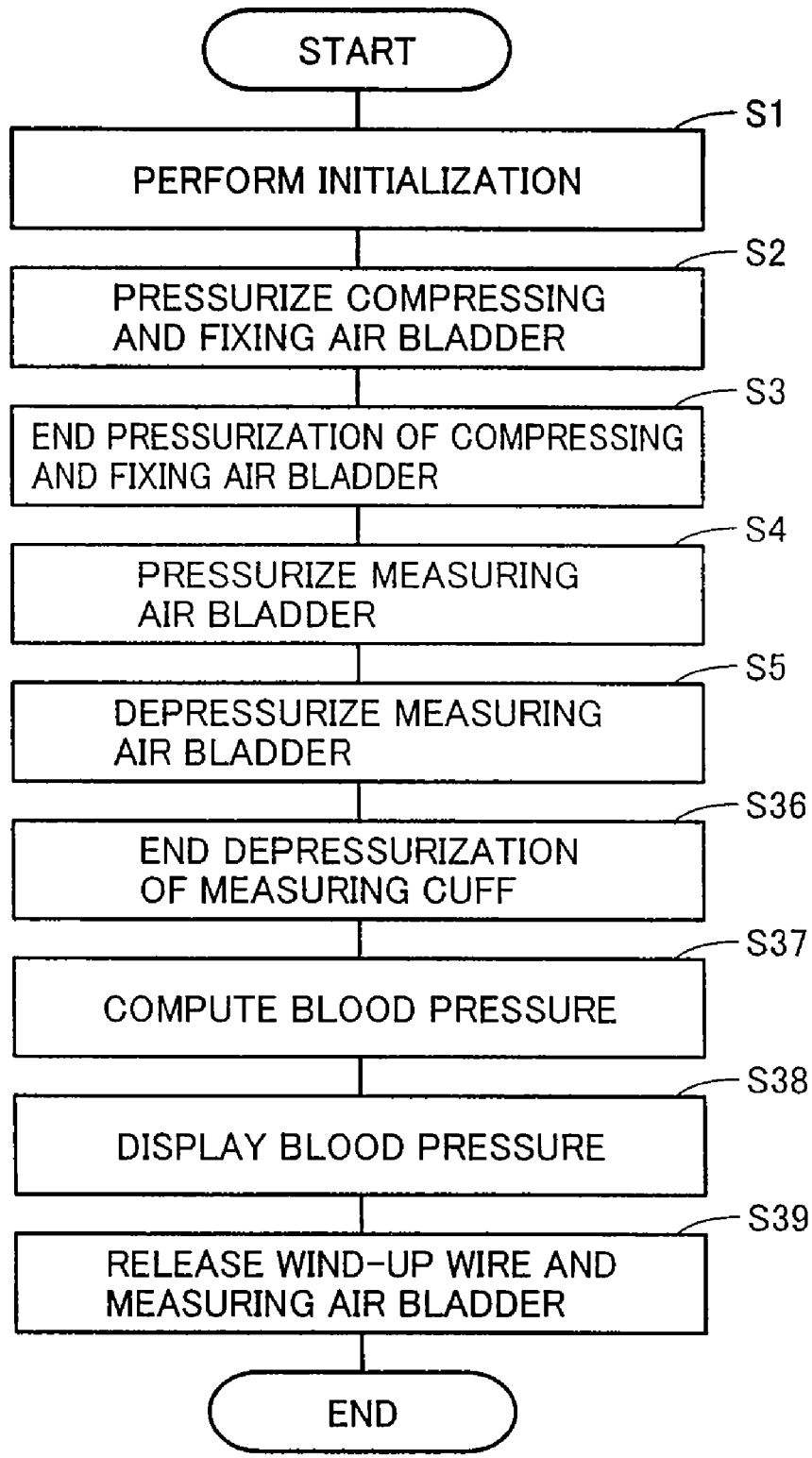
FIG. 12 is a flowchart showing a blood pressure measuring operation in a blood pressure measuring apparatus having a configuration in which two fluid bladders independently provided with a curler interposed therebetween are used for winding a cuff and blood pressure measurement.
Figure 13:
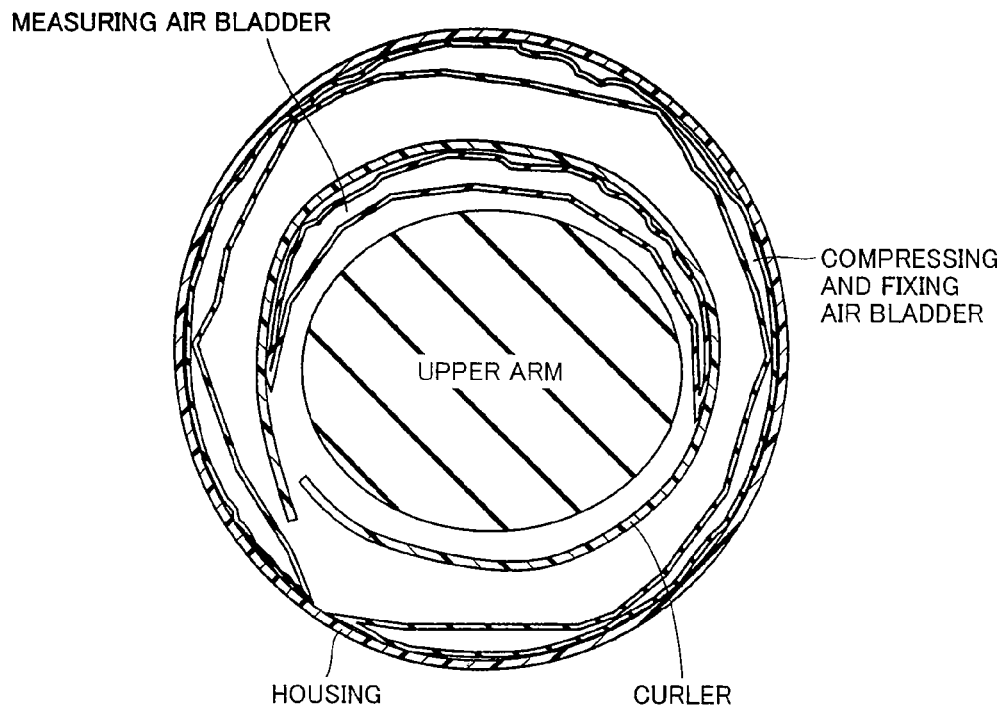
FIG. 13 is a schematic view for illustrating pressurization and depressurization operations of a compressing and fixing air bladder and a measuring air bladder.
Figure 14:
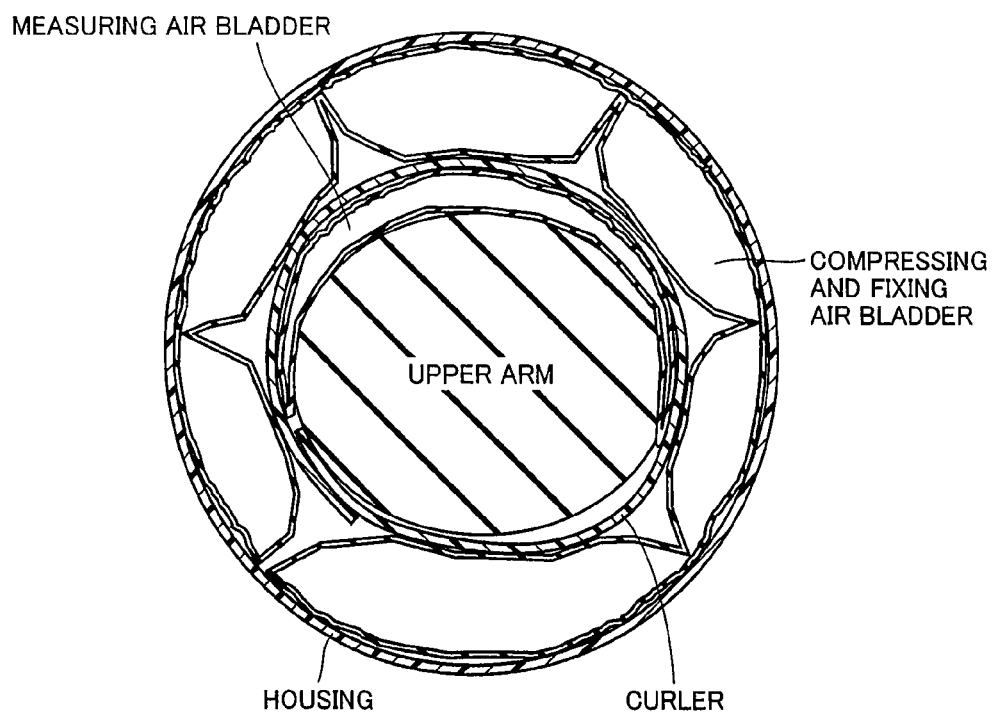
FIG. 14 is a schematic view for illustrating the pressurization and depressurization operations of the compressing and fixing air bladder and measuring air bladder.
Figure 15:
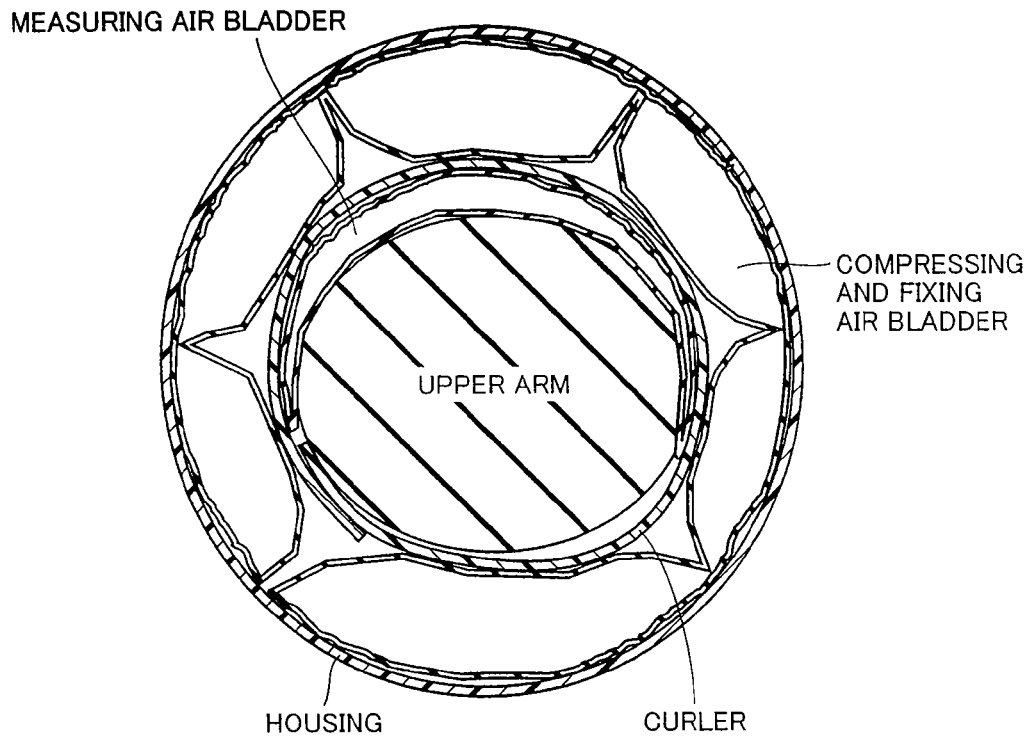
FIG. 15 is a schematic view for illustrating the pressurization and depressurization operations of the compressing and fixing air bladder and measuring air bladder.
Figure 16:
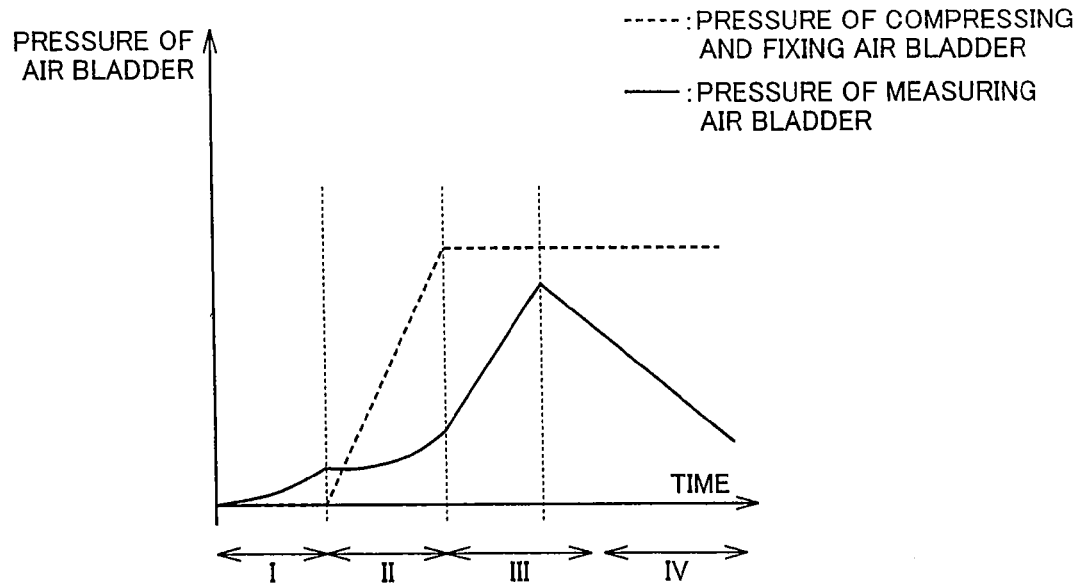
FIG. 16 is a view showing fluctuations in internal pressures of the compressing and fixing air bladder and measuring air bladder in first to fourth procedures.

The blood pressure measuring operation shown in a flowchart of FIG. 11 is performed in blood-pressure meter 1 according to the modification. Referring to FIG. 11, in Step S31, the wire wind-up driving circuit is driven in response to the control signal from CPU 40, and wire wind-up part 82 winds up wire 81 to wind measuring air bladder 13 around the measurement region through curler 10. Similarly to the blood pressure measuring operation described above, CPU 40 monitors the internal pressure of measuring air bladder 13 obtained from pressure sensor 23. When the internal pressure of measuring air bladder 13 reaches a predetermined pressure, wind-up of wire 81 is ended once in Step S32. In Step S33, measuring air bladder 13 is pressurized until the internal pressure of measuring air bladder 13 becomes the pressure enough to press and close the blood vessel. When the internal pressure of measuring air bladder 13 becomes the pressure enough to press and close the blood vessel, the pressurization is ended in Step S34. Depressurization of measuring air bladder 13 is started in Step S35, and the depressurization is ended at a predetermined pressure in Step S36. In Step S37, CPU 40 computes the blood pressure value from the internal pressure of measuring air bladder 13 obtained from pressure sensor 23 during the pressurization in Step S33 or during the depressurization in Step S35, and CPU 40 causes display 4 to display the blood pressure value in Step S38. In Step S39, the air in compressing and fixing air bladder 8 and the air in measuring air bladder 13 are vented to release the compression of the living body.

In blood-pressure meter 1 according to the modification, CPU 40 monitors the internal pressure of measuring air bladder 13 obtained from pressure sensor 23 during the pressurization of measuring air bladder 13 in Step S34 and/or during the depressurization in Step S36, and CPU 40 computes the driving voltage at pump driving circuit 36 in order that wire wind-up part 82 winds or delivers wire 81 to increase or decrease the tightening force when the internal pressure of measuring air bladder 13 reaches the predetermined value.

The state where curler 10 is expanded outside in the radial direction can also be prevented to properly press measuring air bladder 13 against the measurement region by performing the control of the modification, when blood-pressure meter 1 has the configuration shown in FIGS. 10A and 10B. Additionally, the control can be performed such that the volume of measuring air bladder 13 is kept constant as much as possible, and the control can be performed such that the compliance is kept constant as much as possible.

Furthermore, CPU 40 may perform the following control in order to realize the control in which the compliance is kept constant as much as possible during the depressurization.

In Step S13, when the pressurization of compressing and fixing air bladder 8 is completed, CPU 40 estimates the circumferential length of the measurement region based on the time necessary for the pressurization. In Step S14, CPU 40 obtains the maximum pressure value from the change in pressure in pressurizing measuring air bladder 13. In Step S18, CPU 40 obtains the change in pressure in reducing the internal pressure of measuring air bladder 13. In Step S18, CPU 40 performs the control so as to keep the volume of measuring air bladder 13 or the compliance constant according to a predetermined control rule using these values. Specifically, CPU 40 monitors in real time applied voltage data at pump driving circuits 26 and 36 corresponding to the change in supply amount of air, applied voltage data at valve driving circuits 27 and 37 corresponding to the opening and closing states of valves 22 and 32, and the internal pressures of measuring air bladder 13 and compressing and fixing air bladder 8 obtained from pressure sensors 23 and 33. CPU 40 computes the driving voltage of pump 31 to increase or reduce the internal pressure of compressing and fixing air bladder 8 based on these values, and CPU 40 outputs the control signal to pump driving circuit 36 based on the computation result in Step S18. That is, CPU 40 determines the internal pressure of compressing and fixing air bladder 8 corresponding to the internal pressure of measuring air bladder 13 in real time using these pieces of data, and CPU 40 control depressurization of compressing and fixing air bladder 8 such that the internal pressure of measuring air bladder 13 becomes the determined pressure in parallel with the depressurization of measuring air bladder 13 in Step S18.

Figure 21:
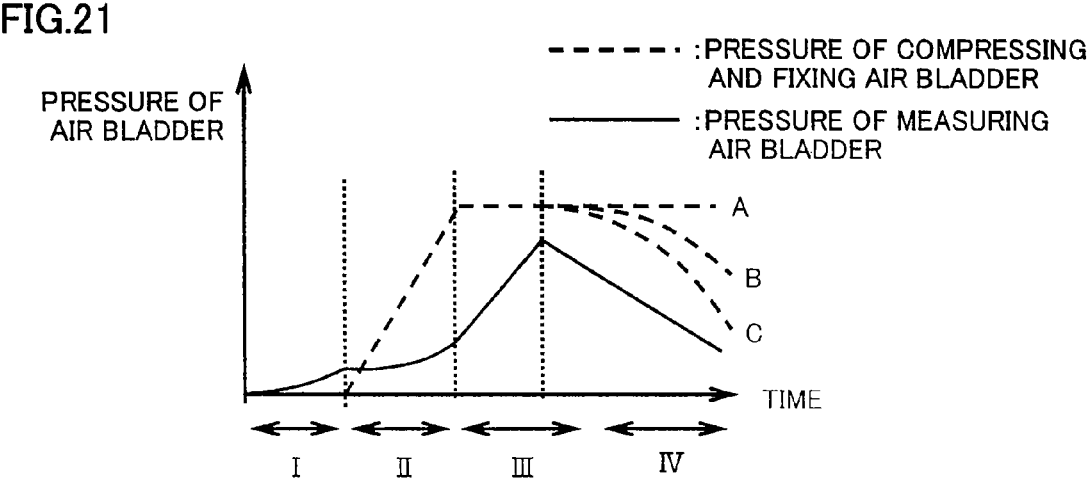
FIG. 21 is a view showing fluctuations in internal pressures of the compressing and fixing air bladder 8 and measuring air bladder 13 in the first to fourth procedures when the pressure of the compressing and fixing air bladder 8 is reduced in the fourth procedure.

As described above, when the volume of measuring air bladder 13 is kept constant in reducing internal pressure P of measuring air bladder 13, the change in compliance is suppressed to a smaller level compared with the normal depressurization in which the volume of measuring air bladder 13 is decreased with reducing internal pressure P of measuring air bladder 13. In such cases, as shown in FIG. 21, the internal pressure of compressing and fixing air bladder 8 is further reduced (B) compared with the normal depressurization (A). When the depressurization is performed while the volume of measuring air bladder 13 is increased, the compliance can further be kept constant. In such cases, as shown in FIG. 21, the internal pressure of compressing and fixing air bladder 8 is further reduced (C) such that the volume of measuring air bladder 13 is not changed compared with the case (B) in which the internal pressure of compressing and fixing air bladder 8 is reduced.

CPU 40 performs the control in Step S18, whereby the pressure pressed from the outside by compressing and fixing air bladder 8 is weakened in reducing the internal pressure of measuring air bladder 13. Therefore, curler 10 is expanded outside, and the volume of measuring air bladder 13 is controlled so as to be kept constant or to be increased. Accordingly, the compliance is kept constant as much as possible in reducing the internal pressure of measuring air bladder 13, and the measurement accuracy can be improved.

Figure 23:
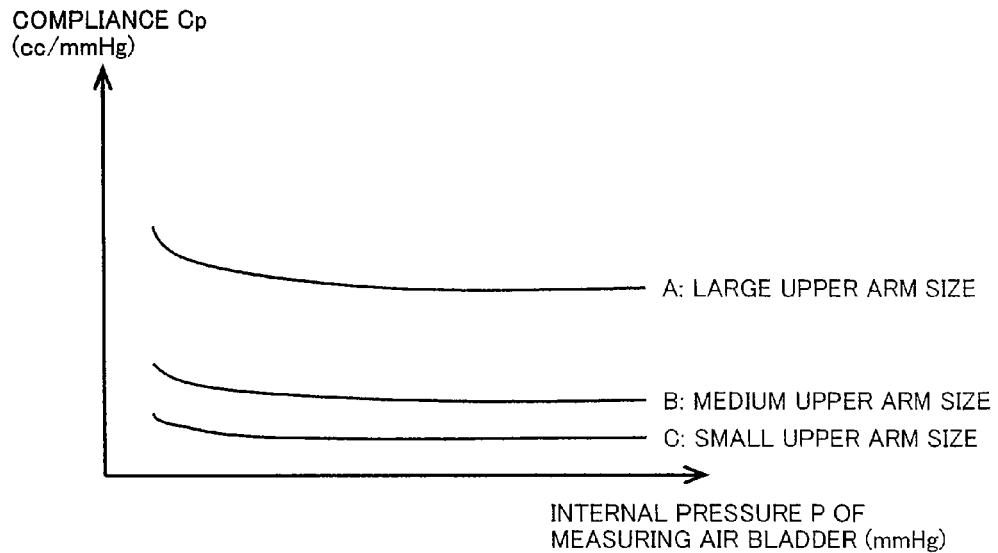
FIG. 23 is a view showing a compliance curve in each thickness of a measurement region.

It is assumed that the circumferential length (i.e., thickness) of the measurement region (for example, upper arm) is classified into multi-stages (for example, large, medium, and small). When the control is performed such that the compliance is kept constant as much as possible during the change in internal pressure of measuring air bladder 13, a compliance curve in each thick of the measurement region is shown in FIG. 23. Referring to FIG. 23, the thick measurement region (A: large upper arm size) has the compliance larger than that of the medium measurement region (B: medium upper arm size), and the thin measurement region (C: small upper arm size) has the compliance smaller than that of the medium measurement region. As a result, referring to FIG. 24, in the case of the thick measurement region (A: large upper arm size), i.e., in the case of the large compliance, the amplitude becomes smaller than that of the medium measurement region (B: medium upper arm size). In the case of the thin measurement region (C: small upper arm size), i.e., in the case of the small compliance, the amplitude becomes larger than that of the medium measurement region. The amplitude of the pulse wave depends on the thickness of the measurement region, i.e., the compliance, which leads to generate an error in the measurement result.

The control which is performed by CPU 40 to match the compliance as much as possible irrespective of the thickness of the measurement region will be described below. Prior to the measurement, CPU 40 detects which classification the thickness of the measurement region belongs to, and the detected classification is used in the control. In the case of the thick measurement region, the space between curler 10 and the measurement region becomes small, and the amount of air of measuring air bladder 13 when optimally wound is smaller than that of the medium measurement region. In the case of the thin measurement region, the space between curler 10 and the measurement region becomes large, and the amount of air of measuring air bladder 13 when optimally wound is larger than that of the medium measurement region. Accordingly, the air is injected into measuring air bladder 13 in a stepwise manner, and the amount of air of measuring air bladder 13 is detected when measuring air bladder 13 is optimally wound, allowing the detection of the classification to which the thickness of the measurement region belongs.

Figure 25:
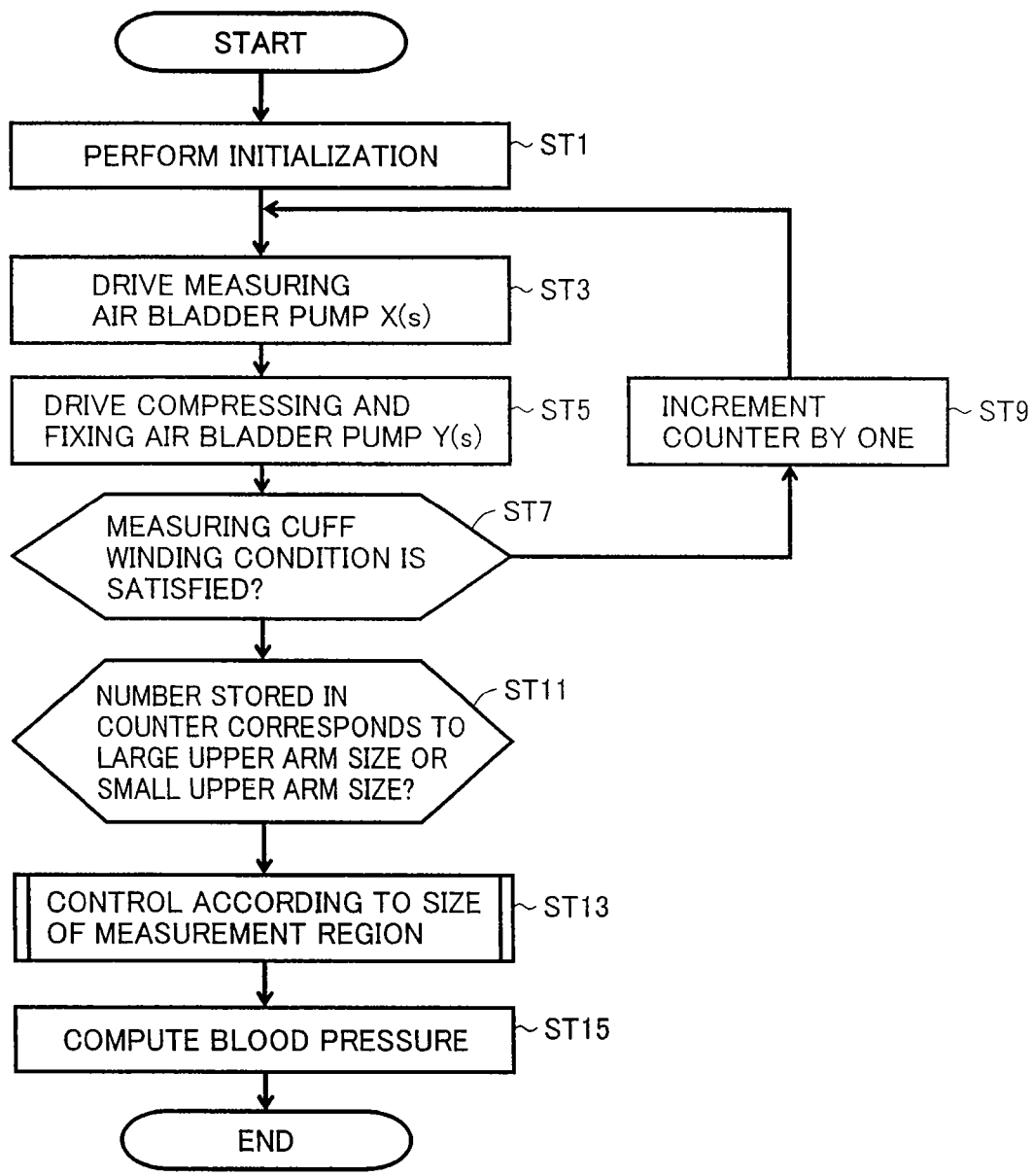
FIG. 25 is a flowchart showing control performed by CPU 40 to match the compliance.

FIG. 25 is a flowchart showing the control performed by CPU 40 to match the compliance as much as possible irrespective of the thickness of the measurement region. The process of FIG. 25 corresponds to the blood pressure measuring operation of FIG. 5 performed by blood-pressure meter 1.

Referring to FIG. 25, the initialization is performed in Step ST1. CPU 40 includes a counter, and CPU 40 sets the counter to zero in the initialization in Step ST1.

CPU 40 outputs the control signal to pump driving circuit 26, CPU 40 drives pump 21 for a period of time X(s) to supply a predetermined amount of air to measuring air bladder 13 (Step ST3), and CPU 40 stops the drive of pump 21 in that state. Then, CPU 40 outputs the control signal to pump driving circuit 36, CPU 40 drives pump 31 for a period of time Y(s) to supply a predetermined amount of air to compressing and fixing air bladder 8 (Step ST5), and CPU 40 stops the drive of pump 31 in that state. After the predetermined amount of air is supplied to compressing and fixing air bladder 8, or while the air is supplied to compressing and fixing air bladder 8, CPU 40 detects whether or not the winding state of measuring air bladder 13 around the measurement region satisfies an optimum winding condition (Step ST7). As described above, the relationship shown in FIG. 8 holds between the winding state of measuring air bladder 13 and the change in internal pressure of measuring air bladder 13. Therefore, the method for monitoring the change in internal pressure of measuring air bladder 13 to detect whether or not the change in internal pressure is included in a predetermined range using a threshold can be cited as one of the methods for detecting the winding state of measuring air bladder 13 in Step ST7. The detection method in Step ST7 is not limited to the particular method, but another method may be used.

As a result of detection in Step ST7, in the state in which the predetermined amount of air is supplied to compressing and fixing air bladder 8 to stop the drive of pump 31 in Step ST5, when CPU 40 does not detect that the winding state of measuring air bladder 13 around the measurement region satisfies the optimum winding condition (NO in Step ST7), CPU 40 increments the counter by one (Step ST9), and CPU 40 returns the process to Step ST3. Then, CPU 40 drives pump 21 for the period of time X(s) to supply the predetermined amount of air to measuring air bladder 13. Steps ST3 and ST5 are repeated until CPU 40 detects that the winding state of measuring air bladder 13 satisfies the optimum winding condition. The predetermined amounts of air are supplied in the stepwise manner to measuring air bladder 13 and compressing and fixing air bladder 8 until the winding state of measuring air bladder 13 satisfies the optimum winding condition.

As a result of detection in Step ST7, in the state in which the predetermined amount of air is supplied to compressing and fixing air bladder 8 to stop the drive of pump 31 in Step ST5, when CPU 40 detects that the winding state of measuring air bladder 13 around the measurement region satisfies the optimum winding condition (YES in Step ST7), CPU 40 reads the number stored in the counter. The number stored in the counter indicates the number of times at which the air is supplied in the stepwise manner to measuring air bladder 13 and compressing and fixing air bladder 8 until the winding state of measuring air bladder 13 satisfies the optimum winding condition.

As described above, the amount of air in measuring air bladder 13 is related to the thickness of the measurement region. Therefore, a relationship between the number of times at which the air is supplied in the stepwise manner to measuring air bladder 13 and the classification to which the thickness of the measurement region belongs is previously stored in memory 41. For example, it is assumed that the measurement region is the thick classification (large upper arm size) in the case of counter 1, i.e., in the case where Steps ST3 and ST5 are performed once respectively, the measurement region is the medium classification (medium upper arm size) in the case of counter 2, i.e., in the case where Steps ST3 and ST5 are performed twice respectively, and the measurement region is the thin classification (small upper arm size) in the case of counter 3, i.e., in the case where Steps ST3 and ST5 are performed triple respectively. The relationship may previously be stored in memory 41, or the relationship may be registered by a user using samples of measurement regions having different thicknesses.

Figure 26:
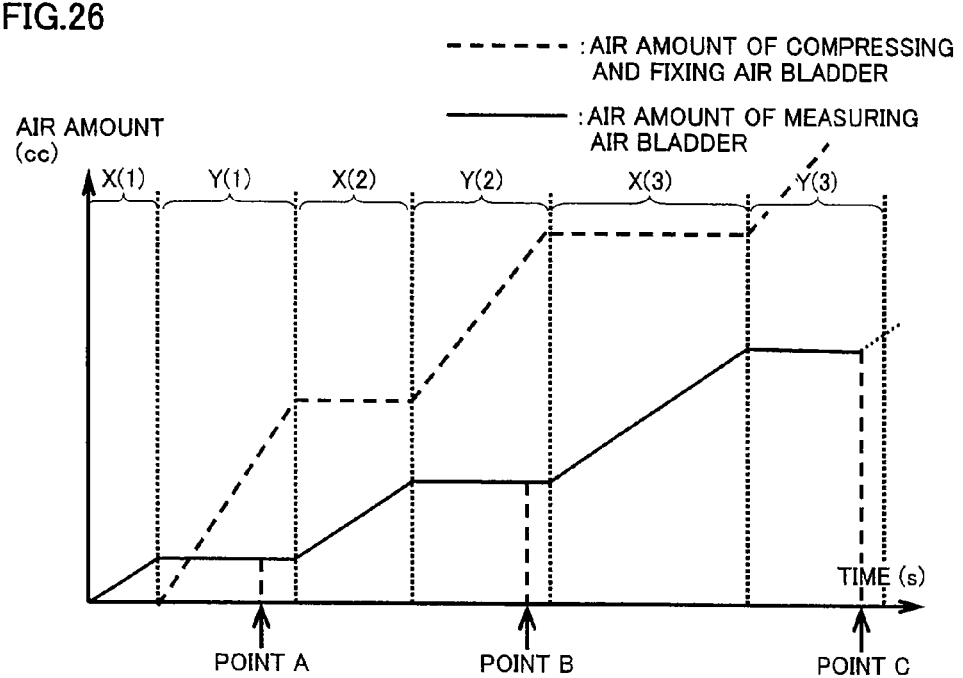
FIG. 26 is a view showing time changes of amounts of air supplied to measuring air bladder 13 and compressing and fixing air bladder 8.

FIG. 26 is a view showing time changes of the amounts of air supplied to measuring air bladder 13 and compressing and fixing air bladder 8 in Steps ST3 to ST7. A method for detecting the classification to which the thickness of the measurement region belongs will be described with reference to FIG. 26. In FIG. 26, the vertical axis indicates the amounts of air supplied to measuring air bladder 13 and compressing and fixing air bladder 8, and the horizontal axis indicates the elapsed time.

Referring to FIG. 26, pump 21 is driven to supply the air to measuring air bladder 13 while pump 31 is stopped for the period of time X(1), and then pump 31 is driven to supply the air to compressing and fixing air bladder 8 while pump 21 is stopped for the period of time Y(1) (Point A of FIG. 26). At this point, when the optimum winding state of measuring air bladder 13 is detected, the classification to which the thickness of the measurement region belongs is detected as the thick classification (large upper arm size). When the optimum winding state of measuring air bladder 13 is detected, the air supply is repeated in the stepwise manner.

Pump 21 is driven to supply the air to measuring air bladder 13 while pump 31 is stopped for the period of time X(2), and then pump 31 is driven to supply the air to compressing and fixing air bladder 8 while pump 21 is stopped for the period of time Y(2) (Point B of FIG. 26). At this point, when the optimum winding state of measuring air bladder 13 is detected, the classification to which the thickness of the measurement region belongs is detected as the medium classification (medium upper arm size). When the optimum winding state of measuring air bladder 13 is detected, the air supply is repeated in the stepwise manner.

Pump 21 is driven to supply the air to measuring air bladder 13 while pump 31 is stopped for the period of time X(3), and then pump 31 is driven to supply the air to compressing and fixing air bladder 8 while pump 21 is stopped for the period of time Y(3) (Point C of FIG. 26). At this point, when the optimum winding state of measuring air bladder 13 is detected, the classification to which the thickness of the measurement region belongs is detected as the thin classification (small upper arm size).

In Step ST11, CPU 40 detects the classification to which the thickness of the measurement region belongs by comparing the numerical value read from the counter and the stored relationship. In the case of the thick classification (large upper arm size) or thin classification (small upper arm size) ("large" or "small" in Step ST11), CPU 40 controls the pressurization of measuring air bladder 13 and compressing and fixing air bladder 8 according to the classification (Step ST13). In the case of the medium classification (medium upper arm size), the control in Step ST13 is skipped. Then, the blood pressure measurement process corresponding to Steps S14 to S21 is performed (Step ST15).

When CPU 40 detects that the classification to which the thickness of the measurement region belongs is the thick classification (large upper arm size) in Step ST11, CPU 40 performs the following control in Step ST13.

Figure 27:
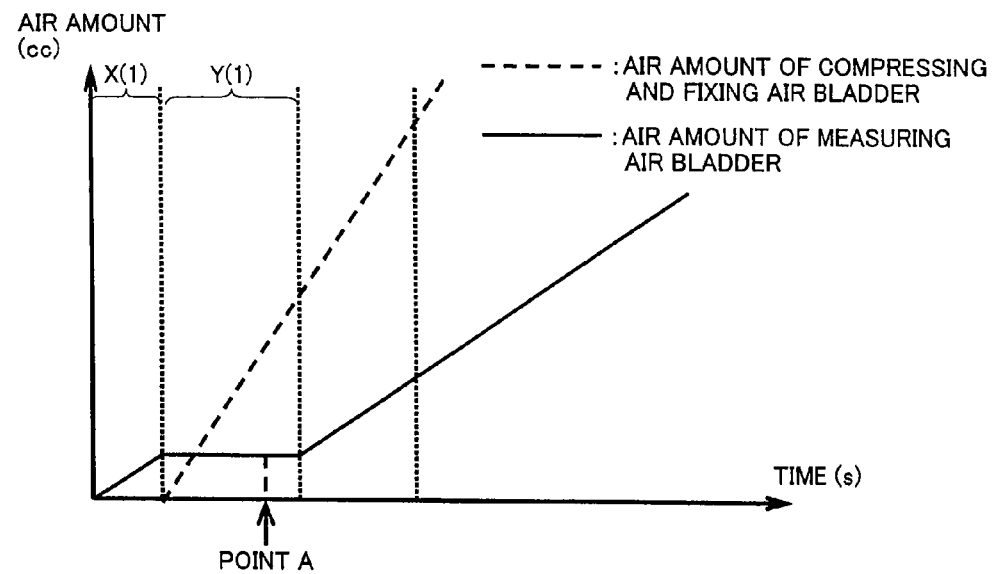
FIG. 27 is a view showing the time changes of the amounts of air supplied to measuring air bladder 13 and compressing and fixing air bladder 8.

FIG. 27 is a view showing the time changes of the amounts of air supplied to measuring air bladder 13 and compressing and fixing air bladder 8 when CPU 40 detects that the classification to which the thickness of the measurement region belongs is the thick classification (large upper arm size) in Step ST11. At the time shown by Point A in FIG. 26, when the optimum winding state of measuring air bladder 13 is detected to detect that that the classification to which the thickness of the measurement region belongs is the thick classification, the flow goes to the processes in Steps ST13 and ST15. When the time Y(1) is elapsed, the pressurization of measuring air bladder 13 and compressing and fixing air bladder 8 is started.

As described above, in the case of the thick measurement region, because the compliance is larger than those of the medium and thin measurement regions, the change in volume $\Delta V$ is larger than that of the small compliance when the change in pressure $\Delta P$ is kept constant. That is, in the case of the same pressure, the change in volume inflated by measuring air bladder 13 is larger than those of the medium and thin thicknesses of the brachia. Therefore, it is necessary that the control be performed such that the inflation of measuring air bladder 13 is suppressed in order to decrease the compliance to the same level as the medium measurement region even in the thick measurement region.

Figure 28:
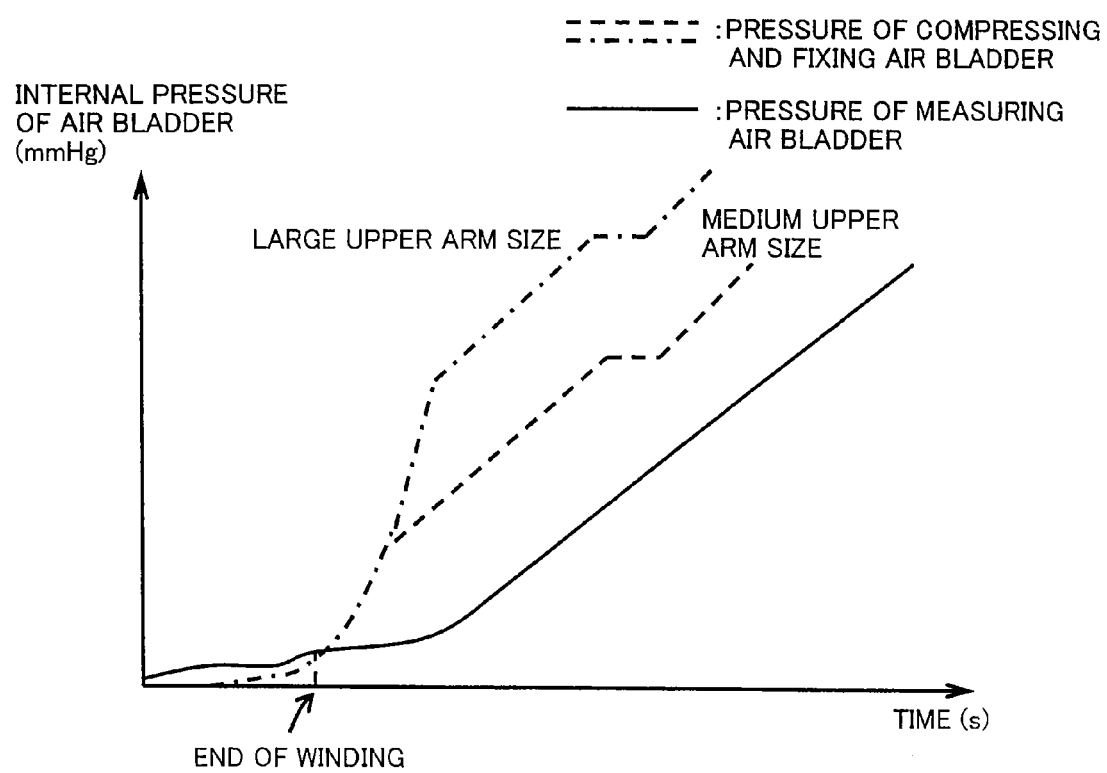
FIG. 28 is a view showing a time change of the internal pressure of measuring air bladder 13.

In the specific control method, when the measurement region is the medium thickness (medium upper arm size), CPU 40 refers to the time change of the internal pressure of measuring air bladder 13 shown in FIG. 28, CPU 40 pressurizes measuring air bladder 13 until the difference in internal pressure between measuring air bladder 13 and compressing and fixing air bladder 8 becomes the predetermined value in Step S15, and CPU 40 starts the pressurization of compressing and fixing air bladder 8 to perform the control such that a difference A in internal pressure between measuring air bladder 13 and compressing and fixing air bladder 8 is kept within a certain degree of range in Step S16 (dot line in FIG. 28). Similarly, in the case of the thick measurement region (large upper arm size), the control is performed such that the difference in internal pressure between measuring air bladder 13 and compressing and fixing air bladder 8 is kept within a certain degree of range. In this case, the pressurization of compressing and fixing air bladder 8 is controlled (alternate long and short dash line of FIG. 28) such that a difference B in internal pressure between measuring air bladder 13 and compressing and fixing air bladder 8 is larger than the difference A in the case where the medium measurement region is the medium thickness (medium upper arm size) (B>A). At this point, the value of the difference B is not limited to a particular value, preferably the difference B is a value several times the difference A.

Figure 29A:
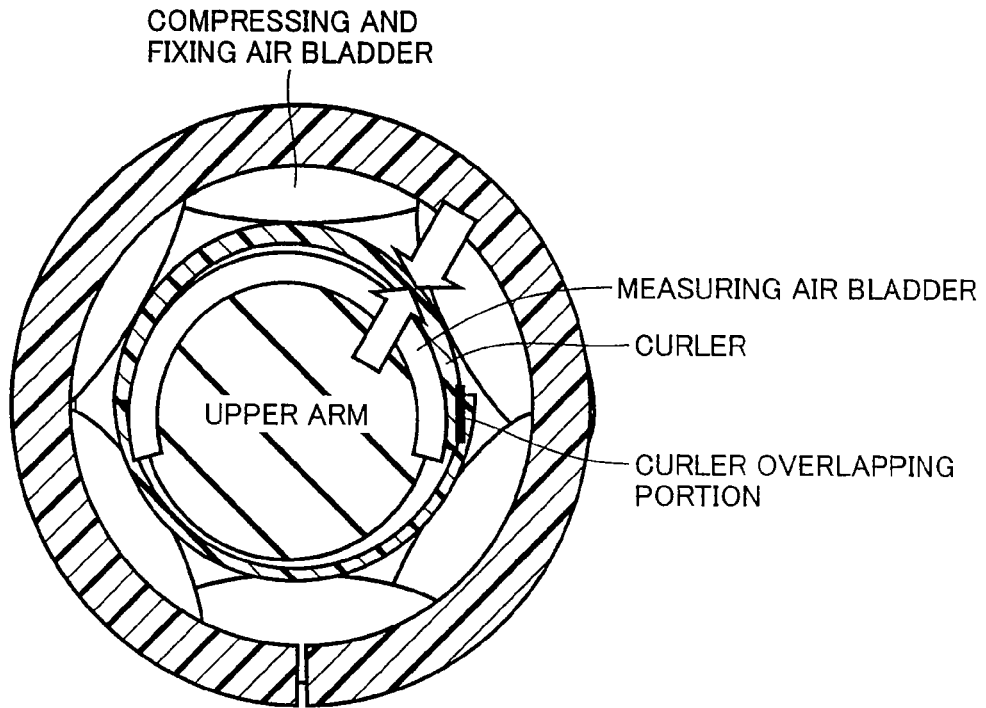
FIG. 29A is a view showing a relationship among measuring air bladder 13, the compressing and fixing air bladder 8, and curler 10.
Figure 29B:
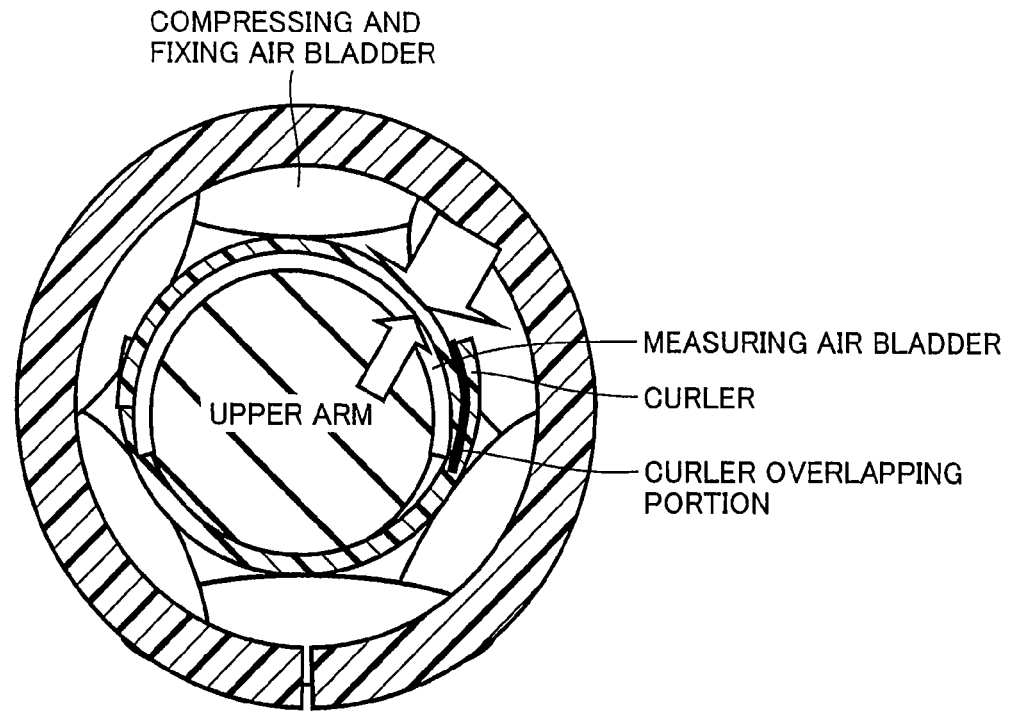
FIG. 29B is a view showing the relationship among measuring air bladder 13, the compressing and fixing air bladder 8, and curler 10.

FIG. 29A is a view showing the relationship among measuring air bladder 13, compressing and fixing air bladder 8, and curler 10 when CPU 40 does not perform the above-described control, and FIG. 29B is a view showing the relationship among measuring air bladder 13, compressing and fixing air bladder 8, and curler 10 when CPU 40 performs the above-described control.

Referring to FIG. 29A, CPU 40 does not perform the above-described control, and it is assumed that the internal pressure of compressing and fixing air bladder 8 is similar to that of the case in which the measurement region has the medium thickness (medium upper arm size). In the case of the thick measurement region (large upper arm size), because the amount of air in measuring air bladder 13 is smaller than that of the medium measurement region (medium upper arm size), the difference A in internal pressure between measuring air bladder 13 and compressing and fixing air bladder 8 also becomes small. Therefore, an overlapping portion of curler 10 is lessened to decrease the frictional force between curler 10 and cloth. Accordingly, measuring air bladder 13 is easily inflated.

Figure 30:
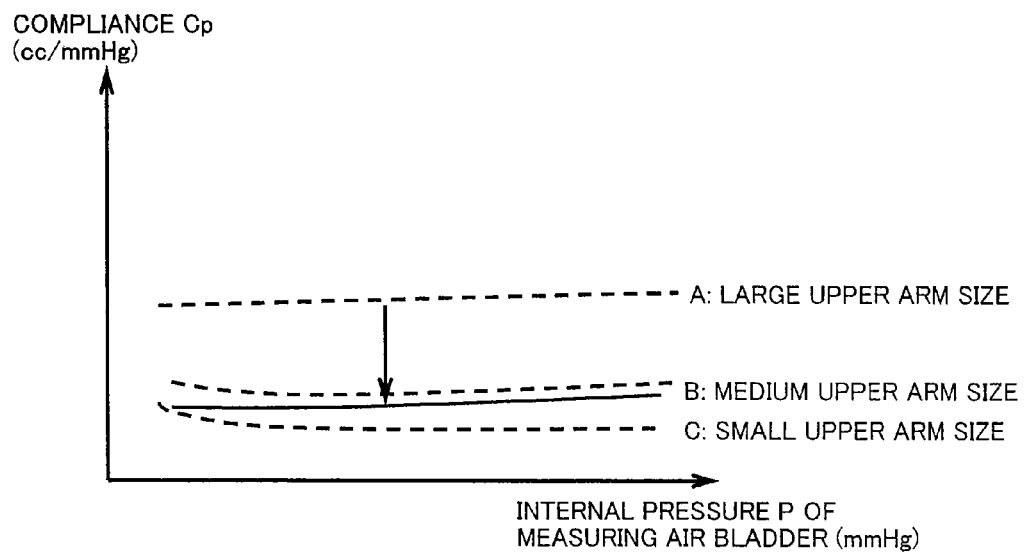
FIG. 30 is a view showing a compliance curve in each thickness of the measurement region.

On the other hand, referring to FIG. 29B, CPU 40 performs the above-described control, the internal pressure of compressing and fixing air bladder 8 is set higher than that of the case in which the measurement region has the medium thickness (medium upper arm size), and the control is performed such that difference B in internal pressure between measuring air bladder 13 and compressing and fixing air bladder 8 is larger than the difference B in the case in which the measurement region has the medium thickness (medium upper arm size) because of the small amount of air in measuring air bladder 13. The difference B larger than the difference A is continuously applied to measuring air bladder 13 to suppress the increase in internal pressure of measuring air bladder 13, and measuring air bladder 13 is pressed and reduced like the case in which the measurement region has the medium thickness (medium upper arm size). That is, as shown in FIG. 30, the compliance is suppressed by the control, and the compliance can be brought close to the compliance in the case in which the measurement region has the medium thickness (medium upper arm size).

When CPU 40 detects that the thickness of the measurement region is the large classification in Step ST11, CPU 40 outputs the control signal to pump driving circuit 36 in Step ST13 such that the internal pressure of compressing and fixing air bladder 8 is increased with a difference shown by an alternate long and short dash line in FIG. 28 with respect to the internal pressure of measuring air bladder 13 in the measurement process in Step S15.

When CPU 40 detects that the thickness of the measurement region is the thin classification (small upper arm size) in Step ST11, CPU 40 performs the following control in Step ST13.

Figure 31:
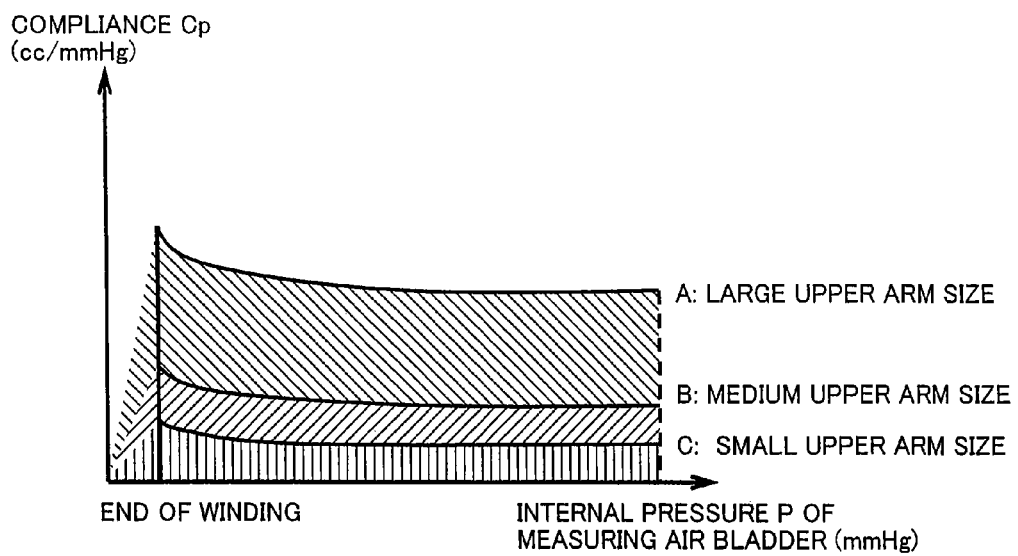
FIG. 31 is a view showing a relationship between the compliance curve in each thickness of the measurement region and the amount of air in measuring air bladder 13.

Because the above-described relationship holds between the thickness of the measurement region and the amount of air in measuring air bladder 13, the relationship shown in FIG. 31 holds between the compliance in each thickness of the measurement region and the amount of air measuring air bladder 13. In FIG. 31, the vertical axis indicates the compliance and the horizontal axis indicates the internal pressure of measuring air bladder 13.

As is clear from FIG. 31, the amount of air in measuring air bladder 13 in each pressure is obtained by integration of the compliance curve up to the pressure. That is, in the case of the thin measurement region, the amount of air in measuring air bladder 13 is smaller than that of the medium thickness.

Figure 32:
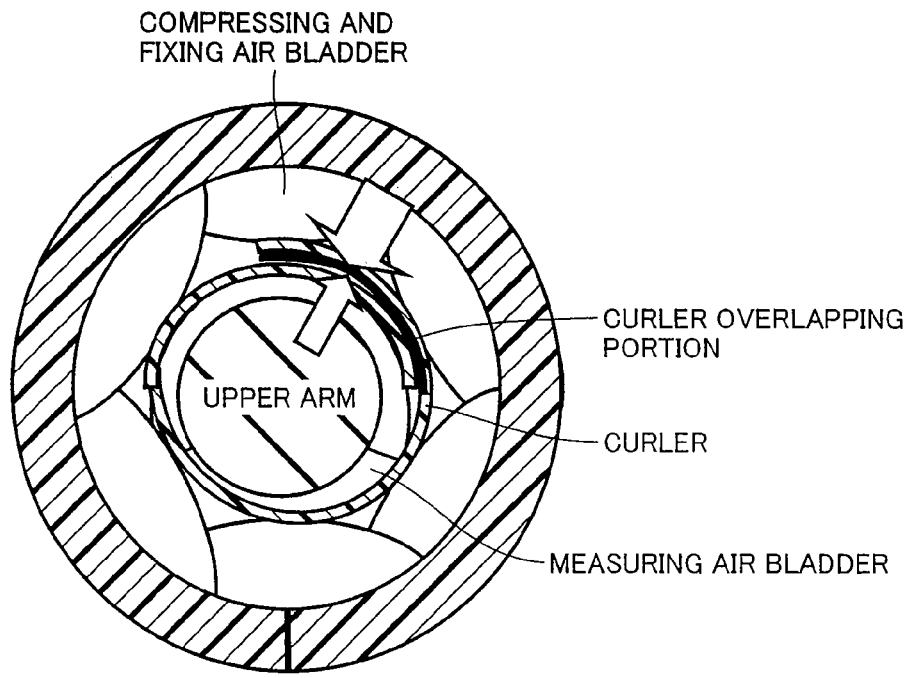
FIG. 32 is a view showing a relationship among measuring air bladder 13, the compressing and fixing air bladder 8, and curler 10.

FIG. 32 is a view showing the relationship among measuring air bladder 13, compressing and fixing air bladder 8, and curler 10 in the case of the thin measurement region. Referring to FIG. 32, in the case of the thin measurement region, the overlapping portion of curler 10 is enlarged compared with the medium measurement region (medium upper arm size). Therefore, the frictional force is increased between curler 10 and cloth. Accordingly, the phenomenon in which measuring air bladder 13 is expanded outside can be suppressed.

When CPU 40 detects that the thickness of the measurement region is the thin classification (small upper arm size) in Step ST11, CPU 40 outputs the control signal to pump driving circuit 26 to supply the difference in Step ST13 such that the amount of air in measuring air bladder 13 becomes identical to the amount of air supplied to measuring air bladder 13 in the case of the medium classification (medium upper arm size) in the measurement process in Step S15. The amount of air in measuring air bladder 13 is previously measured in each thickness of the measurement region, the amount of air corresponding to the thickness of the measurement region is stored in memory 41, and the amount of air supplied is obtained by reading the value.

Figure 33:
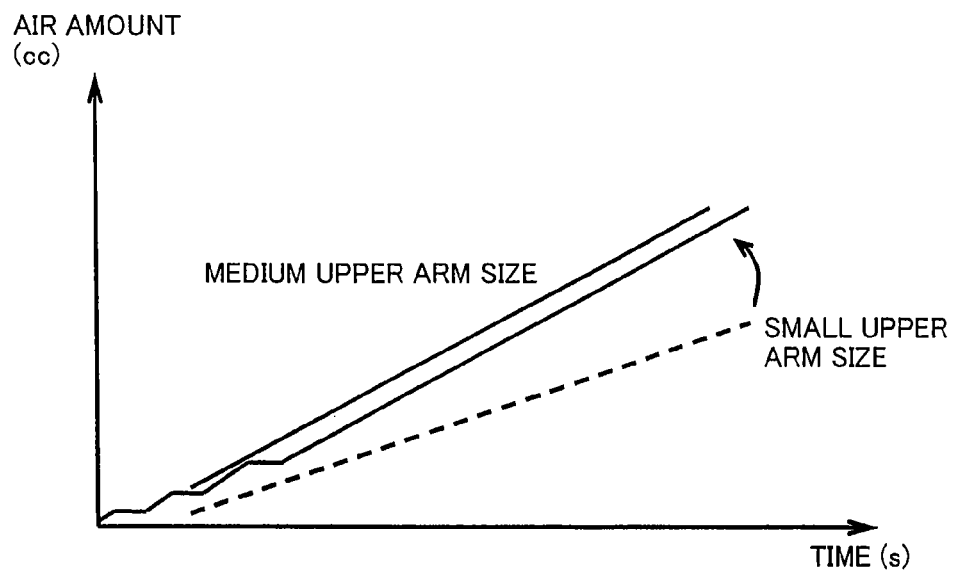
FIG. 33 is a view showing a time change of an amount of air in measuring air bladder 13.

CPU 40 performs the control to supply the air to measuring air bladder 13 as shown in FIG. 33. FIG. 33 is a view showing a time change of the amount of air in measuring air bladder 13. After the air is supplied in the stepwise manner to detect the thickness of the measurement region (time X(1) to X(3) and Y(1) to Y(3)), the air is further supplied to measuring air bladder 13 so as to be brought close to the amount of air supplied to measuring air bladder 13 in the case where the measurement region has the medium thickness. Thus, the control can perform the measurement under the compliance condition similar to that of the case in which the measurement region has the medium thickness (medium upper arm size).

Figure 24:
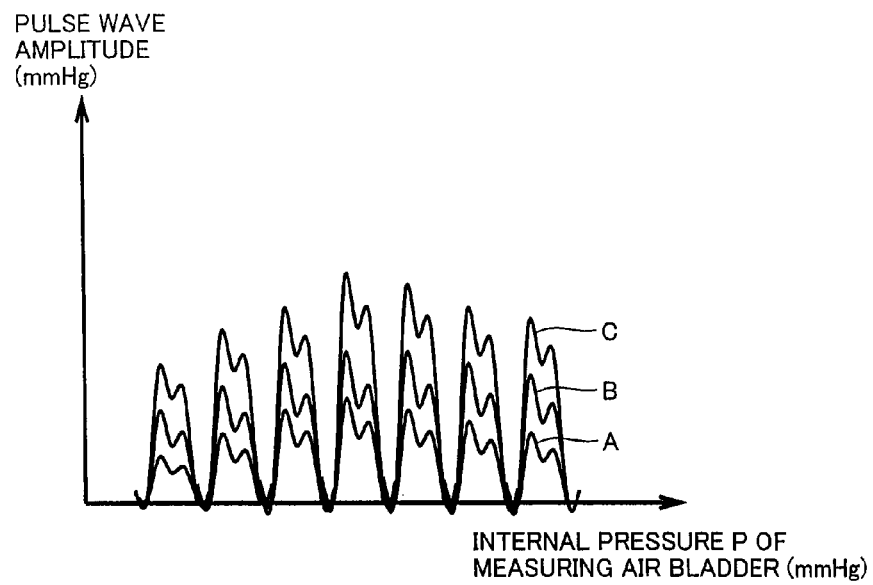
FIG. 24 is a view showing a pulse wave amplitude in each thickness of the measurement region.
Figure 34:
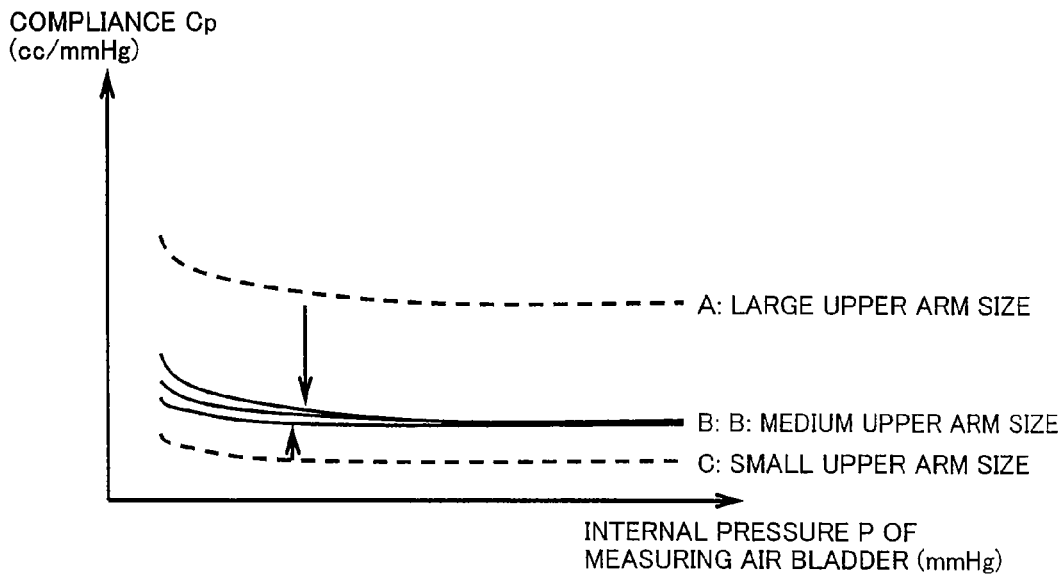
FIG. 34 is a view showing a compliance curve in each thickness of the measurement region.
Figure 35:
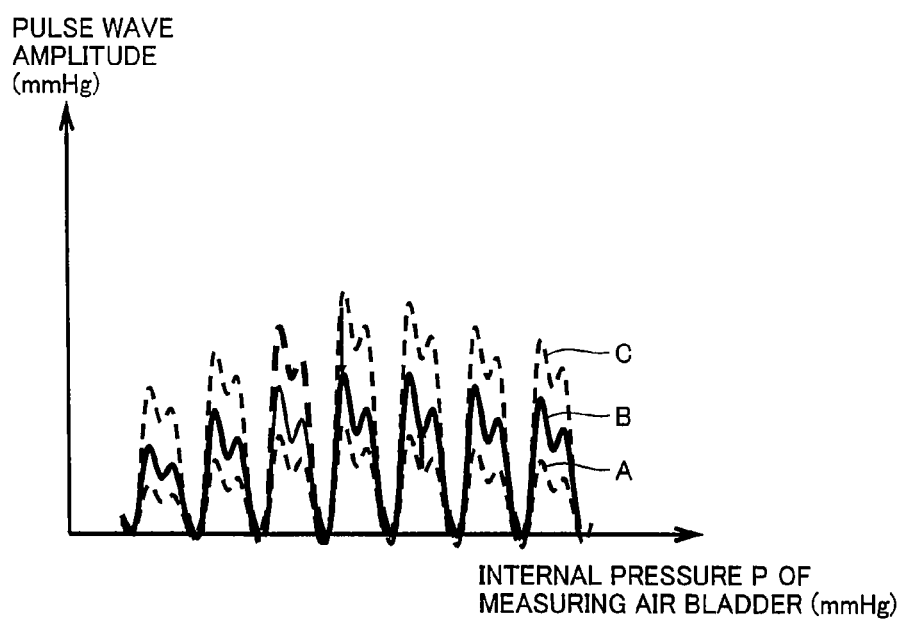
FIG. 35 is a view showing a pulse wave amplitude in each thickness of the measurement region.

Additionally, the control in the case where the thickness of the measurement region is the thick classification (large upper arm size) and the control in the case where the thickness of the measurement region is the thin classification (small upper arm size) can be combined. As shown in FIG. 34, by combining the control in the case of the thick measurement region and the control in the case of the thin measurement region, in the relationship between the thickness of the measurement region and the compliance the compliance in both the thick and thin measurement regions is brought close to the compliance in the medium measurement region, and the blood pressure is measured under the same condition. In FIG. 34, a dashed line indicates the relationship between the compliance and the amount of air in measuring air bladder 13 in the thick measurement region (A: large upper arm size) and the thin measurement region (C: small upper arm size) when CPU 40 does not perform the control as shown in FIG. 23. On the other hand, the relationships in the thick and thin measurement regions are brought close to the case in which the measurement region has the medium thickness (B: medium upper arm size) by the control. As a result, as shown in FIG. 35, the amplitude of the pulse wave obtained from the change in internal pressure of measuring air bladder 13 in each thickness of the measurement region becomes substantially similar to the amplitude in the case where the measurement region has the medium thickness. In FIG. 35, the dashed line indicates the pulse wave amplitude in the thick measurement region (A: large upper arm size) and the thin measurement region (C: small upper arm size) when CPU 40 does not perform the control as shown in FIG. 24. On the other hand, the pulse wave amplitudes in the thick and thin measurement regions are brought close to the case in which the measurement region has the medium thickness (B: medium upper arm size) by the control.

In blood-pressure meter 1 according to the present embodiment, the compliance is hardly changed by the control irrespective of the measurement state in which the measurement region has the different thicknesses, namely, the relationship between the internal pressure and volume of measuring air bladder 13 is hardly changed. Therefore, the pressure pulse wave obtained from the change in internal pressure of measuring air bladder 13 is hardly influence by the difference of the volume of measuring air bladder 13 which is depends on the thickness (i.e., circumference of upper arm) of the measurement region of the subject, so that the accuracy of blood pressure meter measurement can further be improved.

It is to be understood that the above embodiments are disclosed only by way of example and the present invention is not limited to the above embodiments. The scope of the present invention is shown by not the above description but by claims, and it is intended that meanings equivalent to claims and all changes within claims are also included.

The invention claimed is:

1. A blood pressure measuring apparatus comprising:
   a measuring fluid bladder;
   a supply part configured to supply a fluid to said measuring fluid bladder;
   a measuring fluid bladder compressing part configured to compress said measuring fluid bladder in a direction of a measurement region;
   a sensor configured to measure an internal pressure of said measuring fluid bladder;
   a compression degree detector configured to measure a compression degree of said measuring fluid bladder compressed by said measuring fluid bladder compressing part; and
   a first controller configured to control the compression degree of said measuring fluid bladder by said measuring fluid bladder compressing part in at least three phases, wherein
   a first phase occurs when a predetermined amount of fluid is supplied to said measuring fluid bladder at start of measurement,
   a second phase occurs when said measuring fluid bladder is compressed against said measurement region to a predetermined compression degree by said measuring fluid bladder compressing part after said first phase,
   a third phase occurs when a fluid is supplied to said measuring fluid bladder and then is discharged after said second procedure, and
   said first controller controls said compression degree by said measuring fluid bladder compressing part based on the internal pressure of said measuring fluid bladder in said third phase.

2. The blood pressure measuring apparatus according to claim 1, wherein said first controller controls said compression degree by said measuring fluid bladder compressing part based on information indicating a change in internal pressure of said measuring fluid bladder and information indicating a change in supply amount of said fluid in said supply part in said third phase.

3. The blood pressure measuring apparatus according to claim 2, wherein said third phase includes a first step of supplying a fluid to said measuring fluid bladder to pressurize said measuring fluid bladder and a second step of discharging said fluid to depressurize said measuring fluid bladder, and
   said first controller controls said compression degree by said compressing part such that an internal pressure level of said measuring fluid bladder is not larger than said compression degree by said measuring fluid bladder compressing part in said first step.

4. The blood pressure measuring apparatus according to claim 2, wherein said third phase includes a first step of supplying a fluid to said measuring fluid bladder to pressurize said measuring fluid bladder and a second step of discharging said fluid to depressurize said measuring fluid bladder, and
   said first controller controls said compression degree by said measuring fluid bladder compressing part such that said compression degree by said measuring fluid bladder compressing part is not smaller than an internal pressure level of said measuring fluid bladder in said second step.

5. The blood pressure measuring apparatus according to claim 2, wherein said first controller controls said compression degree by said measuring fluid bladder compressing part such that a volume of said measuring fluid bladder is kept constant.

6. The blood pressure measuring apparatus according to claim 2, wherein said first controller controls said compression degree by said measuring fluid bladder compressing part such that compliance of said measuring fluid bladder is kept constant.

7. The blood pressure measuring apparatus according to claim 6, wherein said measuring fluid bladder compressing part controls said compression degree such that said compression degree by said measuring fluid bladder compressing part is increased in a process of pressurizing said measuring fluid bladder and/or said measuring fluid bladder compressing part controls said compression degree such that said compression degree by said measuring fluid bladder compressing part is decreased in a process of depressurizing said measuring fluid bladder.

8. The blood pressure measuring apparatus according to claim 2, wherein said first controller estimates a circumferential length of said measurement region from the information indicating the change in internal pressure of said measuring fluid bladder in said second phase, and
said first controller controls said compression degree in said measuring fluid bladder compressing part according to the circumferential length of said measurement region based on the change in internal pressure of said measuring fluid bladder in said third phase.

9. The blood pressure measuring apparatus according to claim 1, wherein said measuring fluid bladder compressing part is a compressing and fixing fluid bladder located on a side of said measuring fluid bladder while a flexible member is interposed between said measuring fluid bladder compressing part and said measuring fluid bladder.

10. The blood pressure, measuring apparatus according to claim 2, wherein said first controller estimates a circumferential length of said measurement region from the information indicating the change in internal pressure of said measuring fluid bladder in said second phase, and
said first controller controls said compression degree by said measuring fluid bladder compressing part according to the circumferential length of said measurement region in said second phase when estimating that said circumferential length is larger than a predetermined value.

11. The blood pressure measuring apparatus according to claim 10, wherein said third phase starts when a difference between said compression degree in said measuring fluid bladder compressing part and an internal pressure of said measuring fluid bladder in said second phase reaches a predetermined value.

12. The blood pressure measuring apparatus according to claim 2, further comprising a second controller for controlling supply of said fluid in said supply part, wherein
said second controller estimates a circumferential length of said measurement region from the information indicating the change in internal pressure of said measuring fluid bladder in said second phase, and
said second controller controls such that said supply part supplies an amount of fluid corresponding to the circumferential length of said measurement region in said second phase when estimating that said circumferential length is smaller than a predetermined value.

13. The blood pressure measuring apparatus according to claim 12, wherein said amount of fluid corresponding to the circumferential length of said measurement region is a difference between an amount of fluid supplied to said measuring fluid bladder in said third phase when said circumferential length is said predetermined value and an amount of fluid supplied to said measuring fluid bladder in said third phase when said circumferential length is the estimated circumferential length.

* * * * *